(12) United States Patent
Rehli

(10) Patent No.: US 9,074,013 B2
(45) Date of Patent: *Jul. 7, 2015

(54) MEANS AND METHODS FOR DETECTING METHYLATED DNA

(75) Inventor: Michael Rehli, Regensburg (DE)

(73) Assignee: Sequenom, Inc., San Diego, CA (US)

(*) Notice: Subject to any disclaimer, the term of this patent is extended or adjusted under 35 U.S.C. 154(b) by 889 days.

This patent is subject to a terminal disclaimer.

(21) Appl. No.: 11/569,051

(22) PCT Filed: Nov. 28, 2005

(86) PCT No.: PCT/EP2005/012707
§ 371 (c)(1),
(2), (4) Date: Nov. 13, 2006

(87) PCT Pub. No.: WO2006/056480
PCT Pub. Date: Jun. 1, 2006

(65) Prior Publication Data
US 2008/0260743 A1  Oct. 23, 2008

(30) Foreign Application Priority Data

Nov. 29, 2004 (EP) .................................... 04028267

(51) Int. Cl.
| | | |
|---|---|---|
| *C07K 1/00* | (2006.01) | |
| *C07K 14/00* | (2006.01) | |
| *C07K 16/00* | (2006.01) | |
| *C07K 17/00* | (2006.01) | |
| *C07K 14/47* | (2006.01) | |

(52) U.S. Cl.
CPC ......... *C07K 14/4703* (2013.01); *C07K 2319/80* (2013.01); *C07K 2319/20* (2013.01); *C07K 2317/52* (2013.01); *C07K 2319/00* (2013.01); *C12Q 2537/164* (2013.01); *C07K 2319/30* (2013.01)

(58) Field of Classification Search
CPC ..................... C12Q 2537/164; C07K 2319/00; C07K 2319/20; C07K 2319/30; C07K 2319/80; C07K 17/02; C07K 17/14; A61K 38/16
See application file for complete search history.

(56) References Cited

U.S. PATENT DOCUMENTS

| | | | |
|---|---|---|---|
| 4,116,638 A | 9/1978 | Kenoff | |
| 4,608,231 A | 8/1986 | Witty et al. | |
| 5,175,086 A | 12/1992 | Takekawa et al. | |
| 5,399,500 A | 3/1995 | Oppenheimer et al. | |
| 5,441,895 A | 8/1995 | Jakubowicz et al. | |
| 5,639,597 A | 6/1997 | Lauffer et al. | |
| 6,783,759 B2* | 8/2004 | Rosengard ................. | 424/147.1 |
| 6,943,240 B2* | 9/2005 | Bauer et al. ................. | 536/23.1 |
| 2002/0051974 A1 | 5/2002 | Dodge et al. | |
| 2003/0104523 A1* | 6/2003 | Bauer et al. ................. | 435/69.1 |
| 2009/0130659 A1 | 5/2009 | Rehli | |

FOREIGN PATENT DOCUMENTS

| | | |
|---|---|---|
| DE | 19941756 A1 | 3/2001 |
| EP | 0 322 102 A2 | 6/1989 |
| JP | 59-147267 | 8/1984 |
| JP | 61-292556 | 12/1986 |
| JP | 4-136762 | 5/1992 |
| WO | WO 02/101353 A2 | 12/2002 |
| WO | WO 2004/058820 | 7/2004 |
| WO | WO 2004/065625 A1 | 8/2004 |
| WO | WO 2006/056478 | 6/2006 |
| WO | WO 2007/010004 | 1/2007 |
| WO | WO 2007/081791 | 7/2007 |

OTHER PUBLICATIONS

Jones et al. Current trends in molecular recognition and bioseparation. Journal of Chromatography A (1995) 707: 3-22.*
Cross et al. Purification of CpG islands using a methylated DNA binding column. Nature Genetics (1994) 6: 236-244.*
Lopez-Serra et al., Br. J. Cancer, 2008, 98:1881-1885.*
Dhasarathy et al., Mutation Res., 2008, 647:39-43.*
Hendrich et al., Mol. Cell Biol., 1998, 18(11):6538-6547.*
European Search Report dated May 11, 2005, for European Application No. 04 02 8267.
Adorjan, et al., "Tumour class prediction and discovery by microarray-based DNA methylation analysis," *Nucleic Acids Res.*, 30:e21 (2002).
Ballestar, et al., "Methyl-CpG-binding proteins. Targeting specific gene repression," *Eur. J. Biochem.* 268:1-6 (2001).
Bestor, et al., "The DNA methyltransferases of mammals," *Human Molecular Genetics*, 9(16): 2395-2402 (2000).
Brock, et al., "A novel technique for the identification of CpG islands exhibiting altered methylation patterns (ICEAMP)," *Nucleic Acid Res.*, 29:e123 (2001).
Chim, et al., "Epigenetic inactivation of INK4/CDK/RB cell cycle pathway in acute leukemias," *Ann. Hematol.*, 82:738-742 (2003).
Claus, et al., "Epigenetic targets in hematopoietic malignancies," *Oncogene*, 22:6489-6496 (2003).
Costello, et al., "Aberrant CpG-island methylation has non-random and tumour-type-specific patterns," *Nature Genetics*, 25:132-138 (2000).
Costello, et al., "Methylation Matters," *J. Med. Genet.*, 38:285-303 (2001).

(Continued)

Primary Examiner — Hong Sang
(74) Attorney, Agent, or Firm — Grant IP, Inc.

(57) ABSTRACT

The present application relates to a nucleic acid molecule having a nucleotide sequence encoding a bifunctional polypeptide comprising the DNA-binding domain of a protein belonging to the family of Methyl-CpG binding proteins (MBDs) and the Fc portion of an antibody. In addition, vectors and host cells which comprise said nucleic acid molecule and polypeptides which are encoded by said nucleic acid molecule as well as processes for producing said polypeptide are disclosed. Moreover, the present application provides an antibody specifically binding said polypeptide and compositions, in particular diagnostic compositions comprising the nucleic acid molecule(s), vector(s), host cell(s), polypeptide(s) or antibodie(s) of the present application. Furthermore, methods and uses employing the polypeptides of the present invention for detecting methylated DNA, in particular in tumorous tissue or tumor cells are provided.

8 Claims, 12 Drawing Sheets

(56) References Cited

OTHER PUBLICATIONS

Figure 2:
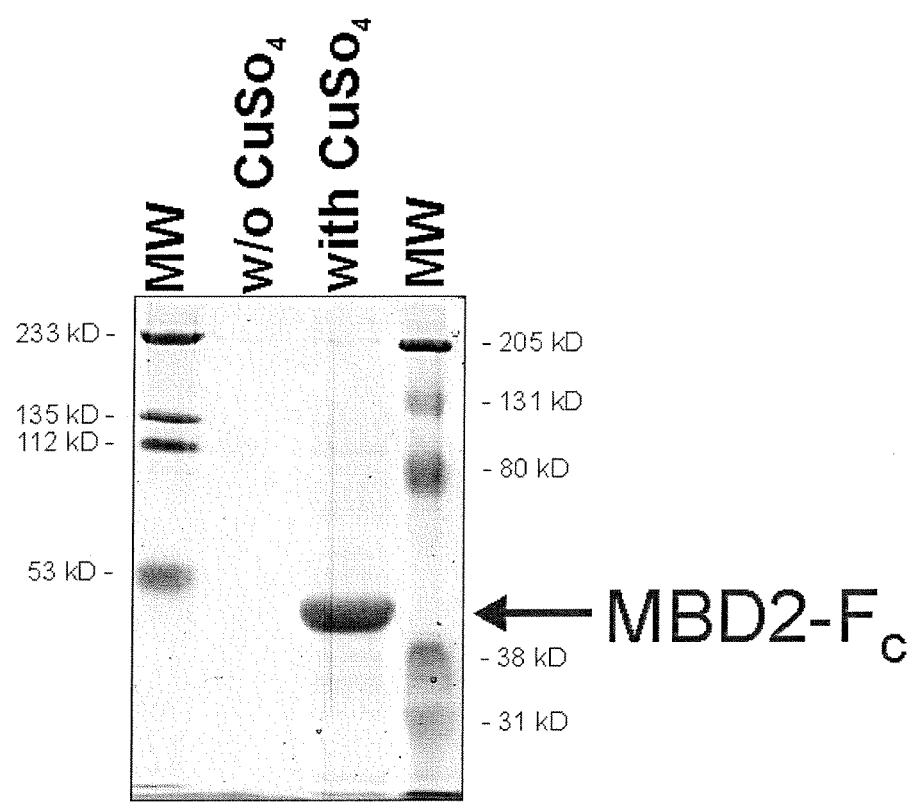

Costello, et al., "Restriction landmark genome scanning," *Methods* 27:144-149 (2002).
Cross, et al., "Purification of CpG islands using a methylated DNA binding column," *Nat. Genet.*, 6:236244 (1994).
Dahl, et al., "DNA methylation analysis techniques," *Biogerontology*, 4:233-250 (2003).
Detich, et al., "Valproate Induces Replication-independent Active DNA Demethylation," *J. Biol. Chem.* 278(30):27586-27592 (2003).
Dodge, et al., "Selective variegated methylation of the p15 CpG island in acute myeloid leukemia," *Int. J. Cancer*, 78:561-567 (1998).
Dodge, et al., "Kg-1 and Kg-1a model the p15 CpG island methylation observed in acute myeloid leukemia patients," *Leuk. Res.* 25:917-925 (2001).
El-Osta, "DNMT cooperativity—the developing links between methylation, chromatin structure and cancer," *BioEssays*, 25:1071-1084 (2003).
Esteller, et al., "A Gene Hypermethylation Profile of Human Cancer," *Cancer Res.*, 61:3225-3229 (2001).
Esteller, et al., "Cancer Epigenetics and Methylation," *Science*, 297:1807-1808 (2002).
Fahrner, et al., "Dependence of Histone Modifications and Gene Expression on DNA Hypermethylation in Cancer," *Cancer Res.*, 62:7213-7218 (2002).
Frommer, et al., "A genomic sequencing protocol that yields a positive display of 5-methylcytosine residues in individual DNA strands," *Proc. Natl. Acad. Sci.*, 89:1827-1831 (1992).
Gagnon, et al., "Interaction of 5-aza-2'-deoxycytidine and depsipeptide on antineoplastic activity and activation of 14-3-3sigma, E-cadherin and tissue inhibitor of metalloproteinase 3 expression in human breast carcinoma cells," *Anticancer Drugs*, 14:193-202 (2003).
Ghoshal, et al., "Inhibitors of histone deacetylase and DNA methyltransferase synergistically activate the methylated metallothionein I promoter by activating the transcription factor MTF-1 and forming an open chromatin structure," *Mol. Cell. Biol.*, 22(23):8302-8319 (2002).
Gitan, et al., "Methylation-specific oligonucleotide microarray: a new potential for high-throughput methylation analysis," *Genome Res.*, 12:158-164 (2002).
Goto, et al., "Regulation of X-chromosome inactivation in development in mice and humans." *Microbiol. Mol. Biol. Rev.*, 62:362-378 (1998).
Haehnel, et al., "Transcriptional regulation of the human toll-like receptor 2 gene in monocytes and macrophages," *J. Immunol.*, 168:5629-5637 (2002).
Hendrich, et al, "The methyl-CpG binding domain and the evolving role of DNA methylation in animals," *Trends Genet.*, 19(5):269-277 (2003).
Herman, et al., "Gene silencing in cancer in association with promoter hypermethylation," *N. Engl. J. Med.*, 349:2042-2054 (2003).
Issa, "Age-related epigenetic changes and the immune system," *Clin. Immunol.*, 109:103-108 (2003).
Issa, "Decitabine," *Curr. Opin. Oncol.*, 15:446-451 (2003).
Issa, et al., "The *Estrogen Receptor* CpG Island Is Methylated in Most Hematopoietic Neoplasms,", *Cancer Res.* 56:973-977 (1996).
Kalebic, "Epigenetic changes: potential therapeutic targets," *Ann. N.Y Acad. Sci.*, 983:278-285 (2003).
Leone, et al., "Inhibitors of DNA methylation in the treatment of hematological malignancies and MDS," *Clin. Immunol.*, 109:89-102 (2003).
Lyons, et al., "Decitabine: Development of a DNA methyltransferase inhibitor for hematological malignancies," *Curr. Opin. Investig. Drugs*, 4:1442-1450 (2003).
Momparler, "Cancer epigenetics," *Oncogene*, 22:6479-6483 (2003).
Ng, et al., "DNA methylation and chromatin modification," *Curr. Opin. Genet. & Dev.*, 9:158-163 (1999).
Plass, "Cancer epigenomics," *Hum. Mol. Genet.* 11(20):2479-2488 (2002).
Razin, "CpG methylation, chromatin structure and gene silencing-a three-way connection," *EMBO J.*, 17:4905-4908 (1998).
Robertson, et al., "DNA methylation in health and disease" *Nat. Rev. Genet.*, 1:11-19 (2000).
Shaker, et al., "Preclinical evaluation of antineoplastic activity of inhibitors of DNA methylation (5-aza-2'-deoxycytidine) and histone deacetylation (trichostatin A, depsipeptide) in combination against myeloid leukemic cells," *Leuk. Res.* 27:437-444 (2003).
Shi, et al., "Oligonucleotide-based microarray for DNA methylation analysis: principles and applications," *J. Cell. Biochem.*, 88:138-143 (2003).
Shiraishi, et al., "Isolation of DNA fragments associated with methylated CpG islands in human adenocarcinomas of the lung using a methylated DNA binding column and denaturing gradient gel electrophoresis," *Proc. Natl. Acad. Sci.*, 96:2913-2918 (1999).
Sims, et al., "Histone lysine methylation: a signature for chromatin function," *Trends in Genet.*, 19(11):629-639 (2003).
Singal, et al., "DNA methylation" *Blood*, 93:4059-4070 (1999).
Smith, et al., "Identification of novel imprinted genes in a genome-wide screen for maternal methylation," *Genome Res.*, 13:558-569 (2003).
Suzuki, et al., "A genomic screen for genes upregulated by demethylation and histone deacetylase inhibition in human colorectal cancer," *Nat. Genet.* 31:141-149 (2002).
Wolffe, et al., "DNA demethylation" *Proc. Natl. Acad. Sci.* 96:5894-5896 (1999).
Yan, et al., "Dissecting Complex Epigenetic Alterations in Breast Cancer Using CpG Island Microarrays," *Cancer Res.* 61:8375-8380 (2001).
Zeschnigk, et al., "Imprinted segments in the human genome: different DNA methylation patterns in the Prader-Willi/Angelman syndrome region as determined by the genomic sequencing method," *Hum. Mol. Genet.* 6(3):387-395 (1997).
PCT International Search Report and the Written Opinion of the International Searching Authority.
International Preliminary Report on Patentability.
Adler, Michael et al., "A real-time immune-PCR assay for routine ultrasensitive quantification of proteins," *Biochemical and Biophysical Research Communications*, vol. 308, No. 2, © 2003 Elsevier Inc., pp. 240-250.
Ballestar, Esteban et al., "Methyl-CpG binding proteins identify novel sites of epigenetic inactivation in human cancer," *The EMBO Journal*, vol. 22, No. 23, © European Molecular Biology Organization, pp. 6335-6345, 2003.
Catt, Kevin et al., "Solid-Phase Radioimmunoassay in Antibody-Coated Tubes," *Science*, vol. 158(808), XP009064766, (Dec. 22, 1967), pp. 1570-1572.
Clouaire, Thomas et al., "Recruitment of MBD1 to target genes requires sequence-specific interaction of the MBD domain with methylated DNA," *Nucleic Acid Research Advance Access*, published Apr. 8, 2010, © The Author(s) 2010, published by Oxford University Press, 15 pages.
Fatemi, Mehrnaz et al., "MBD family proteins: reading the epigenetic code," *Journal of Cell Science*, 119(15):3033-3037, Published by the Company of Biologists 2006, pp. 3033-3037.
Fraga, Mario F. et al., "DNA Methylation: A Profile of Methods and Applications," *BioTechniques*, 33(3):632, 634, 636-649 (Sep. 2002), pp. 632-649.
Hornick, Carole L. et al., "Antibody Affinity-III the Role of Multivalence," *Immunochemistry*, 1972, vol. 9, pp. 325-330.
Klose, Robert J. et al., "DNA Binding Selectivity of MeCP2 Due to a Requirement for A/T Sequences Adjacent to Methyl-CpG," *Molecular Cell*, vol. 19, 667-678, Sep. 2, 2005, Copyright © 2005 by Slsevier Inc., 12 pages.
Notice of Reasons for Rejection issued in Japanese Patent Application No. 2007-541869, mailed on Jul. 5, 2011, pp. 1-10.
PCT International Search Report issued in International Application No. PCT/EP2005/012705, mailed on May 4, 2006, pp. 1-5.
PCT International Search Report issued in PCT/EP2005/012707 mailed Feb. 1, 2008, 13 pages.
PCT Notification Concerning Transmittal of International Preliminary Report on Patentability with PCT International Preliminary

(56) References Cited

OTHER PUBLICATIONS

Report on Patentability and Written Opinion issued in International Application No. PCT/EP2005/012707 dated Mar. 6, 2008, 8 pages.
PCT Written Opinion of the International Searching Authority issued in International Application No. PCT/EP2005/012705, May 4, 2006, pp. 1-6.
Rauch, Tibor et al., "Methylated-CpG island recovery assay: a new technique for the rapid detection of methylated-CpG islands in cancer," *Laboratory Investigation* (2005) 85, © 2005 USCAP, Inc., XP-002375686, pp. 1172-1180.
Sankolli, G.M. et al., "Improvement in the antibody binding characteristics of microtitre wells by pretreatment with anti-IgG Fc immunoglobulin," *Journal of Immunological Methods*, 104 (1987), XP-002375693, pp. 191-194.
Sano, Hiroshi et al., "Detection of heavy methylation in human repetitive DNA subsets by a monoclonal antibody against 5-methylcytosine," *Biochimica et Biophysica Acta*, 951 (1988), © 1988 Elsevier Science Publishers B.V. (Biomedical Division), pp. 157-165.
Shiraishi, Masahiko et al., "Tight Interaction between Densely Methylated DNA Fragments and the Methyl-CpG Binding Domain of the Rat MeCP2 Protein Attached to a Solid Support," *Biol. Chem.*, vol. 380, Sep. 1999, © Copyright by Walter de Gruyter, XP009064603, pp. 1127-1131.
Stratagene Catalog, 1988, pp. 1-2.
Notice of Reasons for Rejection issued in Japanese Patent Application No. 2012-209790, mailed on Apr. 1, 2014.

\* cited by examiner

Figure 1 (I)

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg  cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgccag tgaattttaa cgttgcagga   420
caggatgtgg tgcccgatgt gactagctct ttgctgcagg ccgtcctatc tctggttcc    480
gataagagac ccagaactcc ggcccccac  cgcccaccgc cacccccata catatgtggt   540
acgcaagtaa gagtgcctgc gcatgcccac tgtgcccac  caagagtttt gcatcccata   600
caagtcccca aagtggagaa ccgaaccaat tcttcgcggg cagaacaaaa gcttctgcac   660
acgtctccac tcgaatttgg agccggccgg cgtgtgcaaa agaggtgaat cgaacgaaag   720
acccgtgtgt aaagccgcgt ttccaaaatg tataaaaccg agagcatctg gccaatgtgc   780
atcagttgtg gtcagcagca aaatcaagtg aatcatctca gtgcaactaa aggggggatc   840
cgatctcaat atg aag tta tgc ata tta ctg gcc gtc gtg gcc ttt gtt       889
            Met Lys Leu Cys Ile Leu Leu Ala Val Val Ala Phe Val
              1               5                  10
ggc ctc tcg ctc ggg aga tct cca tgg ccc ggg gta cct act agc acg      937
Gly Leu Ser Leu Gly Arg Ser Pro Trp Pro Gly Val Pro Thr Ser Thr
         15                  20                  25
gag agc ggg aag agg atg gat tgc ccg gcc ctc ccc ccc gga tgg aag      985
Glu Ser Gly Lys Arg Met Asp Cys Pro Ala Leu Pro Pro Gly Trp Lys
 30                  35                  40                  45
aag gag gaa gtg atc cga aaa tct ggg cta agt gct ggc aag agc gat     1033
Lys Glu Glu Val Ile Arg Lys Ser Gly Leu Ser Ala Gly Lys Ser Asp
                 50                  55                  60
gtc tac tac ttc agt cca agt ggt aag aag ttc aga agc aag cct cag     1081
Val Tyr Tyr Phe Ser Pro Ser Gly Lys Lys Phe Arg Ser Lys Pro Gln
             65                  70                  75
ttg gca agg tac ctg gga aat act gtt gat ctc agc agt ttt gac ttc     1129
Leu Ala Arg Tyr Leu Gly Asn Thr Val Asp Leu Ser Ser Phe Asp Phe
         80                  85                  90
aga act gga aag atg atg cct agt aaa tta cag aag aac aaa cag aga     1177
Arg Thr Gly Lys Met Met Pro Ser Lys Leu Gln Lys Asn Lys Gln Arg
     95                 100                 105
ctg cga aac gat cct ctg gcg gcc gcg gat ccc atc gaa ggt cgt ggt     1225
Leu Arg Asn Asp Pro Leu Ala Ala Ala Asp Pro Ile Glu Gly Arg Gly
110                 115                 120                 125
ggt ggt ggt ggt gat ccc aaa tct tgt gac aaa cct cac aca tgc cca     1273
Gly Gly Gly Gly Asp Pro Lys Ser Cys Asp Lys Pro His Thr Cys Pro
                130                 135                 140
ctg tgc cca gca cct gaa ctc ctg ggg gga ccg tca gtc ttc ctc ttc     1321
Leu Cys Pro Ala Pro Glu Leu Leu Gly Gly Pro Ser Val Phe Leu Phe
            145                 150                 155
ccc cca aaa ccc aag gac acc ctc atg atc tcc cgg acc cct gag gtc     1369
Pro Pro Lys Pro Lys Asp Thr Leu Met Ile Ser Arg Thr Pro Glu Val
        160                 165                 170
aca tgc gtg gtg gtg gac gtg agc cac gaa gac cct gag gtc aag ttc     1417
Thr Cys Val Val Val Asp Val Ser His Glu Asp Pro Glu Val Lys Phe
    175                 180                 185
aac tgg tac gtg gac ggc gtg gag gtg cat aat gcc aag aca aag ccg     1465
```

Figure 1 (II)

```
                Asn Trp Tyr Val Asp Gly Val Glu Val His Asn Ala Lys Thr Lys Pro
                190             195                 200                 205
cgg gag gag cag tac aac agc acg tac cgt gtg gtc agc gtc ctc acc              1513
Arg Glu Glu Gln Tyr Asn Ser Thr Tyr Arg Val Val Ser Val Leu Thr
                    210                 215                 220
gtc ctg cac cag gac tgg ctg aat ggc aag gag tac aag tgc aag gtc              1561
Val Leu His Gln Asp Trp Leu Asn Gly Lys Glu Tyr Lys Cys Lys Val
                225                 230                 235
tcc aac aaa gcc ctc cca gcc ccc atc gag aaa acc atc tcc aaa gcc              1609
Ser Asn Lys Ala Leu Pro Ala Pro Ile Glu Lys Thr Ile Ser Lys Ala
                240                 245                 250
aaa ggg cag ccc cga gaa cca cag gtg tac acc ctg ccc cca tcc cgg              1657
Lys Gly Gln Pro Arg Glu Pro Gln Val Tyr Thr Leu Pro Pro Ser Arg
                    255                 260                 265
gat gag ctg acc aag aac cag gtc agc ctg acc tgc cta gtc aaa ggc              1705
Asp Glu Leu Thr Lys Asn Gln Val Ser Leu Thr Cys Leu Val Lys Gly
270                 275                 280                 285
ttc tat ccc agc gac atc gcc gtg gag tgg gag agc aat ggg cag ccg              1753
Phe Tyr Pro Ser Asp Ile Ala Val Glu Trp Glu Ser Asn Gly Gln Pro
                    290                 295                 300
gag aac aac tac aag gcc acg cct ccc gtg ctg gac tcc gac ggc tcc              1801
Glu Asn Asn Tyr Lys Ala Thr Pro Pro Val Leu Asp Ser Asp Gly Ser
                305                 310                 315
ttc ttc ctc tac agc aag ctc acc gtg gac aag agc agg tgg cag cag              1849
Phe Phe Leu Tyr Ser Lys Leu Thr Val Asp Lys Ser Arg Trp Gln Gln
                320                 325                 330
ggg aac gtc ttc tca tgc tcc gtg atg cat gag gct ctg cac aac cac              1897
Gly Asn Val Phe Ser Cys Ser Val Met His Glu Ala Leu His Asn His
                335                 340                 345
tac acg cag aag agc ctc tcc ctg tct ccg ggt aaa tgagctagag                   1943
Tyr Thr Gln Lys Ser Leu Ser Leu Ser Pro Gly Lys
350                 355                 360
ggcccgcggt tcgaaggtaa gcctatccct aaccctctcc tcggtctcga ttctacgcgt            2003
accggtcatc atcaccatca ccattgagtt taaacccgct gatcagcctc gactgtgcct            2063
tctaaggcct gagctcgctg atcagcctcg atcgaggatc cagacatgat aagatacatt            2123
gatgagtttg gacaaaccac aactagaatg cagtgaaaaa aatgctttat ttgtgaaatt            2183
tgtgatgcta ttgctttatt tgtaaccatt ataagctgca ataaacaagt taacaacaac            2243
aattgcattc attttatgtt tcaggttcag ggggaggtgt gggaggtttt ttaaagcaag            2303
taaaacctct acaaatgtgg tatggctgat tatgatcagt cgacctgcag gcatgcaagc            2363
ttggcgtaat catggtcata gctgtttcct gtgtgaaatt gttatccgct cacaattcca            2423
cacaacatac gagccggaag cataaagtgt aaagcctggg gtgcctaatg agtgagctaa            2483
ctcacattaa ttgcgttgcg ctcactgccc gctttccagt cgggaaacct gtcgtgccag            2543
ctgcattaat gaatcggcca acgcgcgggg agaggcggtt tgcgtattgg gcgctcttcc            2603
gcttcctcgc tcactgactc gctgcgctcg gtcgttcggc tgcggcgagc ggtatcagct            2663
cactcaaagg cggtaatacg gttatccaca gaatcagggg ataacgcagg aagaacatg             2723
tgagcaaaag gccagcaaaa ggccaggaac cgtaaaaagg ccgcgttgct ggcgtttttc            2783
cataggctcc gcccccctga cgagcatcac aaaaatcgac gctcaagtca gaggtggcga            2843
aacccgacag gactataaag ataccaggcg tttccccctg gaagctccct cgtgcgctct            2903
cctgttccga ccctgccgct taccggatac ctgtccgcct ttctcccttc gggaagcgtg            2963
gcgctttctc atagctcacg ctgtaggtat ctcagttcgg tgtaggtcgt tcgctccaag            3023
ctgggctgtg tgcacgaacc cccgttcag cccgaccgct gcgccttatc cggtaactat             3083
cgtcttgagt ccaacccggt aagacacgac ttatcgccac tggcagcagc cactggtaac            3143
```

Figure 1 (III)

```
aggattagca gagcgaggta tgtaggcggt gctacagagt tcttgaagtg gtggcctaac  3203
tacggctaca ctagaaggac agtatttggt atctgcgctc tgctgaagcc agttaccttc  3263
ggaaaaagag ttggtagctc ttgatccggc aaacaaacca ccgctggtag cggtggtttt  3323
tttgtttgca agcagcagat tacgcgcaga aaaaaggat ctcaagaaga tcctttgatc  3383
ttttctacgg ggtctgacgc tcagtggaac gaaaactcac gttaagggat tttggtcatg  3443
agattatcaa aaaggatctt cacctagatc cttttaaatt aaaaatgaag ttttaaatca  3503
atctaaagta tatatgagta aacttggtct gacagttacc aatgcttaat cagtgaggca  3563
cctatctcag cgatctgtct atttcgttca tccatagttg cctgactccc cgtcgtgtag  3623
ataactacga tacgggaggg cttaccatct ggccccagtg ctgcaatgat accgcgagac  3683
ccacgctcac cggctccaga tttatcagca ataaaccagc cagccggaag ggccgagcgc  3743
agaagtggtc ctgcaacttt atccgcctcc atccagtcta ttaattgttg ccgggaagct  3803
agagtaagta gttcgccagt taatagtttg cgcaacgttg ttgccattgc tacaggcatc  3863
gtggtgtcac gctcgtcgtt tggtatggct tcattcagct ccggttccca acgatcaagg  3923
cgagttacat gatcccccat gttgtgcaaa aaagcggtta gctccttcgg tcctccgatc  3983
gttgtcagaa gtaagttggc cgcagtgtta tcactcatgg ttatggcagc actgcataat  4043
tctcttactg tcatgccatc cgtaagatgc ttttctgtga ctggtgagta ctcaaccaag  4103
tcattctgag aatagtgtat gcggcgaccg agttgctctt gcccggcgtc aatacgggat  4163
aataccgcgc cacatagcag aactttaaaa gtgctcatca ttggaaaacg ttcttcgggg  4223
cgaaaactct caaggatctt accgctgttg agatccagtt cgatgtaacc cactcgtgca  4283
cccaactgat cttcagcatc ttttactttc accagcgttt ctgggtgagc aaaaacagga  4343
aggcaaaatg ccgcaaaaaa gggaataagg gcgacacgga aatgttgaat actcatactc  4403
ttcctttttc aatattattg aagcatttat cagggttatt gtctcatgag cggatacata  4463
tttgaatgta tttagaaaaa taaacaaata ggggttccgc gcacatttcc ccgaaaagtg  4523
ccacctgacg tctaagaaac cattattatc atgacattaa cctataaaaa taggcgtatc  4583
acgaggccct ttcgt                                                   4598
```

MEANS AND METHODS FOR DETECTING METHYLATED DNA

The present application relates to a nucleic acid molecule having a nucleotide sequence encoding a bifunctional polypeptide comprising the DNA-binding domain of a protein belonging to the family of Methyl-CpG binding proteins (MBDs) and the Fc portion of an antibody. In addition, vectors and host cells which comprise said nucleic acid molecule and polypeptide which are encoded by said nucleic acid molecule as well as processes for producing said polypeptides are disclosed. Moreover, the present application provides an antibody specifically binding said polypeptide and compositions, in particular diagnostic compositions comprising the nucleic acid molecule(s), vector(s), host cell(s), polypeptide(s) or antibodie(s) of the present application. Furthermore, methods and uses employing the polypeptides of the present invention for detecting methylated DNA, in particular in tumorous tissue or tumor cells are provided.

The information to make the cells of all living organisms is contained in their DNA. DNA is made from 4 bases abbreviated as G, A, T, and C, and is built like a very long ladder with pairs of these letter making up each of the "rungs" of the ladder. The letter G pairs with C and A with T. Strings of these pairs store information like a coded message, with the information to make specific molecules grouped into regions called genes. Every cell of diploid animals contains two copies of every one of our genes, with one copy of each gene coming from the mother and one copy from the father. (The only exceptions to this rule are genes on chromosomes that determine whether organisms develop as a "male" or a "female".)

DNA Methylation and Gene Regulation

Apart from the four bases—adenine, guanine, cytosine and thymine—that "spell" our genome, there also is a fifth base which is produced by the modification of the post-replicative DNA. DNA methyl transferases (DNMTs) can catalyse the transfer of a methyl group from the methyl donor S-adenosylmethionine to the cytosine ring, and thereby produce the base 5-methylcytosine. Specific cytosine residues are modified in mammals, which precede a guanosine residue in the DNA sequence (CpG dinucleotide) (Singal, Blood 93 (1999), 4059-4070); Robertson, Nat. Rev. Genet. 1 (2000), 11-19; Ng, Curr. Opin. Genet. Dev. (2000), 158-163; Razin, EMBO J. 17 (1998), 4905-4908). The methylation of CpG dinucleotides generally correlates with stable transcriptional repression and presumably leads to the fact that large parts of the non-coding genome and potentially harmful sequences such as transposons, repeats or viral inserts are not transcribed. It is interesting that CpG dinucleotides are very unevenly distributed in the genome (Singal (1999), loc. cit., Robertson (2000), loc. cit., Ng (2000), loc. cit., Razin (1998), loc. cit.). A large part of the genome contains much fewer CpGs than is statistically expected. This is presumably due to the fact that 5-methylcytosine deaminates comparatively easily to thymidine, which, in the course of evolution, leads to a relative decrease in the number of CpG dinucleotides. There are, however, again and again, larger numbers of CpGs distributed within the genome, so-called CpG islands. These regions often contain transcription initiation points and gene promoters and are generally not methylated in contrast to the CpGs which are not associated with CpG islands. In normal cells, the methylation of CpG islands has been observed only in exceptional cases such as the inactivation of the second copy of the x-chromosome in female cells and the parental imprinting genome (Singal (1999), loc. cit., Robertson (2000), loc. cit., Ng (2000), loc. cit., Razin (1998), loc. cit.).

Regulation of DNA Methylation

It is only partly understood how DNA methylation patterns are established in the course of the embryogenesis and how the CpG methylation is maintained and regulated in the genome (Singal (1999), loc. cit., Ng (2000), loc. cit., Razin (1998), loc. cit.). In mammal species, there are three DNA methyl transferases known (DNMT1, 3a and 3b) which catalyse the DNA methylation process. The corresponding share that each DNMT contributes to the maintenance and regulation of the CpG methylation must, however, still be clarified. Yet, all three enzymes are obviously essential to embryogenesis, the corresponding knockout mice die in utero or shortly after birth (Bestor, Hum. Mol. Genet. 9 (2000), 2395-2402; El Osta, Bioessays 25 (2003), 1071-1084). In the meantime, the connection between DNA methylation, modifications of the chromatin structure and certain histone modifications has been shown several times. The methylation of DNA mostly correlates with histone deacetylation and methylation of the lysine 9 residue at histone H3 (Sims, Trends Genet. 19 (2003), 629-639, Fahrner, Cancer Res. 62 (2002), 7213-7218). Accordingly, DNMTs are associated with histone acetylases (HDACs) or co-repressor complexes. It is also hardly known how methyl groups are removed from CpG residues. In proliferating cells, the DNA methylation can probably also take place passively during replication. There are, however, also examples of DNA demethylation in post-mitototic cells which can be explained by the existence of an active, yet unknown demethylase (Wolffe, Proc. Natl. Acad. Sci. 96 (1999), 5894-5896).

CpG Methylation and Gene Silencing

Methylation of promoters (but not of non-regulating sequences) correlates with stable, transcriptional repression (Singal (1999), loc. cit., Ng (2000), loc. cit., Razin (1998), loc. cit.). The repressive properties of 5-methylcytosine can be mediated by two mechanisms. Firstly, the DNA methylation can directly impair the binding of transcription factors. The second possibility, which is likely to be responsible for the largest part of repression, is the recruitment of methyl-CpG-binding proteins (MBPs) (Ballestar, Eur. J. Biochem. 268 (2001), 1-6). MBPs such as MECP2 or MBD2 (a component of the MeCP1 complex) are accompanied by co-repressor complexes and HDACs which have a repressive effect and are responsible for the formation of dense chromatin structures inaccessible to transcription factors (heterochromatin) (Ballestar (2001), loc. cit.).

Epigenetic Changes in Tumorigenesis

It keeps becoming clearer that the formation of tumours is supported not only by genetic lesions (e.g. mutations or translocations) but also by epigenetic changes. An abnormal chromatin structure or DNA methylation can influence the transcriptional status of oncogenes or tumour suppressor genes and can promote tumour growth. Changes in the DNA methylation include either the loss of methylation in normally methylated sequences (hypomethylation) or the methylation of normally unmethylated sequences (hypermethylation) (Roberston (2000), loc. cit., Herman, N. Engl. J. Med. 349 (2003), 2042-2054; Momparler, Oncogene 22 (2003), 6479-6483; Esteller, Science 297 (2002), 1807-1808; Plass, Hum. Mol. Genet. 11 (2002), 2479-2488).

Hypomethylation

A global DNA hypomethylation has been described for almost all kinds of tumours. In tumour tissue, the content in 5-methylcytosine is reduced compared to normal tissue with the major share of demethylation events being found in repetitive satellite sequences or in centromer regions of the chromosomes. However, in single cases, the demethylation and activation of proto-oncogenes such as, e.g., bcl-2 or c-myc have also been described (Costello, J. Med. Genet. 38 (2001), 285-303).

Hypermethylation of CpG Islands

CpG islands in general exert gene regulatory functions. This is why a change in the status of methylation correlates mostly directly with a change in the transcriptional activity of the locus concerned (Robertson (1999); Herman (2003); Esteller (2002); Momparler (2003); Plass (2002), all loc. cit.). Most CpG islands are present in unmethylated form in normal cells. In certain situations, CpG islands can, however, also be methylated in gene regulatory events. The majority of CpG islands of the inactivated X-chromosome of a female cell are, for example, methylated (Goto, Microbiol. Mol. Biol. Rev. 62 (1998), 362-378). CpG islands can be methylated also in the course of normal aging processes (Issa, Clin. Immunol. 109 (2003), 103-108).

It is in particular in tumours that CpG islands which are normally not methylated can be present in a hypermethylated form. In many cases, genes affected by the hypermethylation encode proteins which counteract the growth of a tumour such as, e.g., tumour suppressor genes. The following Table lists examples of genes for which it could be shown that they can be inactivated in tumours through the epigenetic mechanism of hypermethylation.

TABLE

Hypermethylated genes in tumours (examples)

| | gene | chromosome | function |
|---|---|---|---|
| cell cycle control | p16 | 9p21 | cycline-dependent kinase inhibitor |
| | p15 | 9p21 | cycline-dependent kinase inhibitor |
| | Rb | 13q14 | cell cycle inhibition |
| | p73 | 1p36 | p53-like protein |
| DNA repair | MLH1 | 3p21 | DNA mismatch repair protein |
| | GSTPI | 11q13 | inhibitor of oxidative DNA damage |
| | O6-MGMT | 10q26 | DNA methyltransferase |
| | BRCA1 | 17q21 | DNA repair protein |
| apoptosis | TMS-1/ASC | 16p12-p11 | adaptor for caspase 1 |
| | caspase 8 | 2q33-q34 | PCD initiator (Fas, Trail, TNF, . . . ) |
| | DAPK1 | 9q34 | PCD by IFNγ |
| invasion/ architecture | E-cadherin | 16q22 | adhesion molecule |
| | VHL | 3p26-p25 | angiogenesis-promoting protein |
| | TIMP-3 | 22q12-q13 | metalloproteinase inhibitor |
| | THBS1 | 15q15 | angiogenesis inhibitor |
| growth factor response | ER-α | 6q25 | estrogen receptor |
| | RAR-β | 3p24 | retinoic acid receptor |
| | SOCS-1 | 16p13 | neg. regulator in the JAK/STAT signal path |

Reasons for the tumour-specific hypermethylation are almost unknown. Interestingly, certain kinds of tumours seem to have their own hypermethylation profiles. It could be shown in larger comparative studies that hypermethylation is not evenly distributed but that it occurs depending on the tumour. In cases of leukaemia, mostly other genes are hypermethylated compared to, for instance, colon carcinomas or gliomas. Thus, hypermethylation could be useful for classifying tumours (Esteller, Cancer Res. 61 (2001), 3225-3229; Costello, Nat. Genet. 24 (2000), 132-138).

In many cases, hypermethylation is also combined with an increased activity of HDACs. After treatment with demethylated substances (e.g. 5-azacytidine), methylated genes could only be reactivated after also using HDAC inhibitors (such as, e.g., trichostatin A (TSA)) (Suzuki, Nat. Genet. 31 (2002), 141-149; Ghoshal, Mol. Cell. Biol. 22 (2002), 8302-8319; Kalebic, Ann. N.Y. Acad. Sci. 983 (2003), 278-285).

Most analyses suggest that the DNA methylation is dominantly repressed and that it cannot be reversed by a treatment with HDAC inhibitors such as TSA (Suzuki (2002); Ghoshal (2002), loc. cit.). There are, however, also more recent indications that valproate, a HDAC inhibitor which is already used in clinics, can lead to the demethylation of DNA (Detich, J. Biol. Chem. 278 (2003), 27586-27592). However, no systematic analyses have so far been carried out in this respect.

Clinical Approaches for Reversing Epigenetic Changes

While genetic causes of cancer (such as, e.g., mutations) are irreversible, epigenetic changes contributing their share to the tumorigenesis might possibly be reversible. Thus, the possible treatment of epitgenetic changes offers new possibilities of therapy for the treatment of neoplasias (Herman (2003); Momparler (2003); Plass (2002), all loc. cit.; Leone, Clin. Immunol. 109 (2003), 89-102; Claus, Oncogene 22 (2003), 6489-6496).

More than 20 years ago, 5-azacytidine has already been developed as an anti-neoplastic medicament and used without the molecular effect of the substance being known. Nowadays, it is already used successfully in a further developed form (Deoxy-5-azacytidine, Decitabine) for the treatment of myelodysplastic syndromes and secondary leukaemia (Leone (2003), loc. cit.; Lyons, Curr. Opin. Investig. Drugs 4 (2003), 1442-1450; Issa, Curr. Opin. Oncol. 15 (2003), 446-451). Due to the in vitro observation that HDAC inhibitors can support the reactivation of methylated promoters and can act synergistically with demethylated substances, at present pilot studies are carried out throughout the world, combining the use of both classes of substances (Kalebic (2003); Claus (2003), loc. cit.; Gagnon, Anticancer Drugs 14 (2003), 193-202; Shaker, Leuk. Res. 27 (2003), 437-444).

Detection Methods for the Analysis of CpG Methylation

The development of detection methods for the analysis of genomic CpG methylation has mainly gained importance due to the fact that it has been found that changes in the CpG methylation pattern can be associated with diseases such as cancer. At present, there are mainly techniques known which are used for the detection of the CpG methylation of known gene loci (Dahl, Biogerontology 4 (2003), 233-250). Methods allowing an analysis of the CpG methylation throughout the genome are less established. In the following, the most common methods for analysis of CpG methylation together with their main fields of application are summarised.

Use of Methylation-Sensitive Restriction Enzymes for the Detection of CpG Methylation The methylation status of specific CpG dinucleotides can be determined using isoschizomers of bacterial restriction endonucleases which are characterised by different sensitivities vis-à-vis 5-methylcytosine. Examples thereof are the enzymes HpaII and MspI—both cut CCGG sequences, HpaII however only if the internal cytosine is not methylated. Some assays are based on the use of methylation-sensitive restriction enzymes, said assays being used for both the analysis of individual genes and analysis of the CpG methylation throughout the genome. The fragments of a methylation-sensitive restriction digestion are mostly detected by means of Southern blot or a genomic PCR of the region flanking the restriction site (Dahl (2003), loc. cit.). All analyses of the CpG methylation throughout the genome, which have been published up to today, use methylation-sensitive restriction enzymes as a component of the method. Restriction Landmark Genomic Scanning (RLGS) (Costello, Methods 27

(2002), 144-149), for instance, uses a kind of two-dimensional agarose gel electrophorese in which every dimension is digested with a different methylation-sensitive restriction enzyme to identify differences in the CpG methylation of two DNA populations. Methylated CpG Island Amplification (MCA) enriches fragments with methylated SmaI restriction sites and uses LM-PCR for enriching the fragments. Such amplification products have already been successfully analysed by means of Representational Difference Analysis (RDA) (Smith, Genome Res. 13 (2003), 558-569) or CpG island microarrays (Yan, Cancer Res. 6 (2001), 8375-8380).

With regard to the analysis of the CpG methylation throughout the genome, all assays that are based on methylation-sensitive restriction enzymes have disadvantages. In order to carry out the assays in an optimal way, it has, amongst others, to be guaranteed that all restriction digestions are completed. The greatest disadvantage is that the analyses merely inform on the methylation status of the cytosine residues which have been recognised by the methylation-sensitive restriction enzymes used. The selection of the restriction enzymes automatically limits the number of detectable sequences—a neutral analysis of the CpG methylation is therefore not possible.

Bisulfate Treatment for the Analysis of the CpG Methylation

The treatment of double-stranded genomic DNA with sodium bisulfate leads to the deamination of unmethylated cytosine residues into uracil residues and to the formation of two single strands that are no longer complementary. During this treatment, 5-methyl cytosine is maintained. The differences in sequence produced in this way form the basis of the differentiation between methylated and unmethylated DNA (Frommer, Proc. Natl. Acad. Sci. 889 (1992), 1827-1831). DNA treated with bisulfite can be used directly in PCR in which uracil residues (previously unmethylated cytosine) and thymidine residues are amplified as thymidine and only 5-methylcytosine residues are amplified as cytosine residues. Depending on the application, the primers used for the PCR differentiate between methylated and unmethylated sequences or amplify fragments independently of the methylation status. PCR fragments which have been amplified using non-discriminating primers can, for instance, be sequenced directly to determine the share in methylated and unmethylated CpGs. Further methods make use of the physical differences of such PCR fragments (melting behaviour, single-strand conformation, restriction sites for restriction enzymes, etc.) for determining the degree of methylation (Dahl (2003), loc. cit.). Other methodical approaches utilise the differences in sequence for the specific amplification of methylated and unmethylated sequences by discriminating primers or probes (methylation-specific PCR, methylight PCR) (Dahl (2003), loc. cit.). Bisulfite-inducing differences in sequence of PCR products can also be found by means of methylation-specific oligonucleotide (MSO) micro-arrays (Shi, J. Cell. Biochem. 88 (2003), 138-143; Adorjan, Nucleic Acid Res. 30 (2002), e21; Gitan, Genome Res. 12 (2002), 158-164).

In contrast to the methylation-sensitive restriction enzymes, the DNA treated with bisulfite can provide information on the methylation status of several CpG residues in an amplified genomic fragment. The treated DNA is not suitable for analyses throughout the genome presumably due to its reduced complexity and its high degree of denaturation.

Further Methods for the Detection of CpG Methylation

Antibodies against 5-methyl cytosine recognise CpG methylation in denatured, single-stranded DNA are used mainly for the immunohistochemical staining of the CpG methylation on the chromosomes of individual, fixed cells. Yet, these antibodies are not suitable for enriching methylated sequences.

Already in 1994, the laboratory of A. Bird developed a method for enriching methylated DNA fragments by means of affinity chromatography (Cross, Nat. Genet.6 (1994), 236-244). A recombinant MECP2 bound to a matrix was used for binding the methylated DNA. Since then this technique has been used, improved and combined with further techniques by other working groups (Shiraishi, Proc. Natl. Acad. Sci. 96 (1999), 2913-2918; Brock, Nucleic Acid. Res. 29 (2001), E123). The binding of strongly or less strongly methylated genomic sequences to an affinity matrix depends on the salt concentration which makes it possible to separate the CpG islands with dense methylation from other sequences with a lower methylation density. The disadvantage of this affinity chromatography is the large amount of genomic DNA required (50-100 µg) and the relatively time-consuming procedure.

In view of the foregoing, it is evident that methylation of CpG dinucleotides is an important epigenetic mechanism for controlling transcriptional activity of a cell. Generally, methylation of CpG dinucleotides correlates with transcriptional inactivity. Yet, during normal or degenerated differentiation processes the methylation pattern of genloci may change. Accordingly, the reversal of normal methylation patterns during tumorigenesis can lead to an abnormal repression (or activation) of genes, for instance, tumor suppressor genes or oncogenes, respectively, and, thus, leading to tumorigenesis. Hence, the detection of CpG methylated DNA and thus the identification of misregulated tumor-suppressor genes and/or oncogenes is of outmost clinical interest. As mentioned above, the prior art describes different approaches for the detection of methylated DNA which, however, suffer from certain shortcomings. For example, the methods of the prior art may not allow a neutral, genome-wide analysis of CpG methylated DNA or may not be suitable for high-through put applications or may not reliable detect CpG methylated DNA, particularly if only low amounts of DNA can be made subject of an analysis. Thus, there is still a need for further means and methods for detecting methylated DNA which may overcome the shortcomings and drawbacks of the prior art. Accordingly, the technical problem underlying the present invention is to comply with the needs described above. The solution to this technical problem is achieved by providing the embodiments characterized in the claims.

Accordingly, a first aspect of the present invention is a polynucleotide having a nucleotide sequence encoding a bifunctional polypeptide comprising the DNA-binding domain of a protein belonging to the family of Methyl-CpG binding proteins (MBDs) and an Fc portion of an antibody. Said DNA-binding domain is described herein below. It may in an alternative embodiment of the present invention also be a fragment thereof as long as said fragment is capable of binding methylated DNA, preferably CpG methylated DNA. In a preferred embodiment of the present invention, the nucleic acid molecule comprising a nucleotide sequence encoding the bifunctional polypeptide of the present invention further comprises a nucleotide sequence encoding a linker polypeptide. Preferably, the nucleotide sequence encoding said linker polypeptide is disposed in the polynucleotide encoding the bifunctional polypeptide of the present invention between the nucleotide sequence encoding the MBD and an Fc portion such that it results in a fusion between said MBD, linker polypeptide and Fc portion. A "fusion" refers to a co-linear linkage of two or more proteins or fragments thereof via their individual peptide backbones through genetic expression of a nucleic acid molecule encoding those proteins. Thus, preferred fusion proteins include the DNA-binding domain of an MBD or fragment thereof, wherein said fragment has preferably the activity of binding methylated DNA, preferably CpG methylated DNA, covalently linked to the linker polypeptide which is itself covalently linked to an Fc portion of an antibody as is described herein.

Said polypeptide linker is preferably a flexible linker. Preferably, it comprises plural, hydrophilic, peptide-bonded amino acids and connects the C-terminal end of the DNA-binding domain of an MBD and the N-terminal end of an Fc portion. Optionally, the polypeptide of the present invention contains a protease cleavage site preceeding the Fc portion which allows the cut off said Fc portion if desirable. Protease cleavage sites are, for example, a thrombin cleavage site.

Preferably, said polypeptide linker comprises a plurality of glycine, alanine, aspartate, glutamate, proline, isoleucine and/or arginine residues. It is further preferred that said polypeptide linker comprises a plurality of consecutive copies of an amino acid sequence. Usually, the polypeptide linker comprises 1 to 20, preferably 1 to 19, 1 to 18, 1 to 17, 1 to 16 or 1 to 15 amino acids although polypeptide linkers of more than 20 amino acids may work as well. In a preferred embodiment of the invention said polypeptide linker comprises 1 to 14 amino acid residues. In a particularly preferred embodiment of the present invention said polypeptide linker in the polypeptide of the invention comprises 14 amino acids. As demonstrated in the appended examples, said polypeptide linker advantageously comprises the amino acid sequence "AAADPIEGRGGGGG" which is also shown in SEQ ID NO: 2 (FIG. 1) from positions 116 to 129.

The polypeptide of the present invention may optionally comprise a tag at its N- and/or C-Terminus. A "tag" is an amino acid sequence which is homologous or heterologous to an amino acid sequence sequence to which it is fused. Said tag may, inter alia, facilitate purification of a protein or facilitate detection of said protein to which it is fused. Preferably, said tag is selected from the group consisting of a HA-tag, myc6-tag, flag-tag, strep-tag, strepII-tag, TAP-tag, HAT-tag, chitin binding domain (CBD), maltose-binding protein, immunoglobulin A (IgA), His-6-tag, glutathione-S-transferase (GST) tag, intein and streptavidie binding protein (SBP) tag.

CpG islands frequently contain gene promoters and transcription start sites and are usually unmethylated in normal cells. Methylation of CpG-islands is associated with transcriptional repression. In cancer, the methylation of CpG-island promoters leads to the abnormal silencing of tumor-suppressor genes, contributing to the pathogenesis of the disease. So far, the investigation of aberrant CpG-island methylation in human cancer has primarily taken a candidate gene approach which, however, suffers from several shortcomings. These are, for example, incomplete coverage of genloci involved in tumorigenesis which may be subject of methylation, either hyper- or hypomethylation or incomplete analysis of genloci due to limited means and methods when using, for example, Restriction Landmark Genomic Scanning (RLGS). To allow an unbiased, genome wide detection of CpG-methylated DNA, the present invention provides means and methods that allow the separation and detection of CpG-methylation, without applying, for example, methylation-sensitive restriction endonucleases or bisulfite-treatment. These means and methods are, inter alia, based on a methyl-CpG-binding, antibody-like protein that efficiently binds CpG-methylated DNA. As described herein, the methyl-CpG-binding, antibody-like protein comprises a DNA-binding domain of a protein belonging to the family of Methyl-CpG binding proteins (MBDs) and the constant portion of an antibody.

It was surprisingly found that a recombinant methyl-CpG-binding, antibody-like protein can preferably bind CpG methylated DNA in an antibody-like manner. That means, the methyl-CpG-binding, antibody-like protein of the present invention has a high affinity and high avidity to its "antigen" which is preferably DNA that is preferably methylated at CpG dinucleotides. Without being bound by theory the high affinity and avidity of the polypeptide of the present invention for its "antigen" is caused by the unique structure of said methyl-CpG-binding, antibody-like protein. The unique structure of the polypeptide of the present invention is assumed to be achieved by the presence of the constant region of an antibody and, thus, renders said polypeptide to be preferably a bifunctional molecule. The constant regions are believed to form disulfide-bonds between immunoglobulin heavy chains of the constant regions of each of two polypeptide molecules of the present invention. Accordingly, preferably an antibody-like structure is formed closely resembling the structure of an antibody. Again, without being bound by theory it is assumed that this structure lends, for example, stability on the polypeptide of the present invention. This is because, it is described in the art that proteins fused to a constant region of an antibody may confer a higher stability and half-life of the said protein. In addition, it is believed that the antibody-like structure caused by the intermolecular interaction of the constant regions brings the methyl-DNA-binding domain of one polypeptide of the present invention in close proximity to the methyl-DNA-binding domain of another polypeptide of the present invention. This allows bivalent interactions between the methyl-DNA-binding proteins and methylated DNA. Accordingly, the polypeptide of the present invention is preferably capable of binding to its antigen via two methyl DNA-binding domains which are part of the polypeptide of the present invention. The high affinity binding of the polypeptide of the present invention is, inter alia, also achieved by using preferably methyl-DNA-binding domains of proteins instead of the full-length methyl-DNA-binding protein containing domains for the interaction with other proteins that may, however, disturb or interfere the unique applicability as described herein which are known to specifically bind to methylated DNA, preferably, CpG methylated DNA, rather than to unmethylated DNA. The use of the methyl-DNA-binding domain, moreover, guarantees that indeed methylated DNA is bound since the detection is direct and not indirect. Most prior art methods can only indirectly detect methylated DNA by PCR.

These properties award the polypeptide of the present invention to be a reliable and easy applicable diagnostic tool for, inter alia, isolating, purifying enriching and/or detecting methylated DNA even if said DNA is only present in very small amounts, e.g., about more than 10 ng, less than 10 ng, less than 7.5 ng, less than 5 ng, less than 2.5 ng or about 1 ng as described herein. Accordingly, due to its antibody-like structure the polypeptide of the present invention is a robust molecule rendering it to be applicable, for instance, for various applications including multi-step procedures in a single tube assay. For example, specific separation and detection of CpG-methylated DNA was demonstrated using reverse South-Western blot analysis and methyl-CpG immunoprecipitation (MCIp). The latter technique, combined with real-time PCR, e.g. LightCycler PCR, allows the sensitive detection of CpG-island methylation of candidate CpG-island promoters from as little as, e.g., 1 ng total genomic DNA. MCIp-generated genomic DNA-fragments can be easily amplified, labelled and used for CpG-island microarray hybridisation. Using the techniques described herein, it is possible to generate genome-wide profiles of aberrant CpG-island methylation in human cancer and, for example, to identify (a) tumor-suppressor gene(s) or further suppressor gene activities.

Before the present invention is described in detail, it is to be understood that this invention is not limited to the particular methodology, protocols, bacteria, vectors, and reagents etc. described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

The term "nucleic acid molecule" when used herein encompasses any nucleic acid molecule having a nucleotide sequence of bases comprising purine- and pyrimidine bases which are comprised by said nucleic acid molecule, whereby said bases represent the primary structure of a nucleic acid molecule. Nucleic acid sequences include DNA, cDNA, genomic DNA, RNA, synthetic forms, for example, PNA, and mixed polymers, both sense and antisense strands, or may contain non-natural or derivatized nucleotide bases, as will be readily appreciated by those skilled in the art. The polynucleotide of the present invention is preferably composed of any polyribonucleotide or polydeoxyribonucleotide, which may be unmodified RNA or DNA or modified RNA or DNA. For example, the polynucleotide can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. The polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, the term "nucleic acid molecules" embraces chemically, enzymatically, or metabolically modified forms.

The term "polypeptide" when used herein means a peptide, a protein, or a polypeptide which are used interchangeable and which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. As mentioned the terms polypeptide and protein are often used interchangeably herein. The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, for instance, PROTEINS—STRUCTURE AND MOLECULAR PROPERTIES, 2nd Ed., T. E. Creighton, W.H. Freeman and Company, New York (1993); POST-TRANSLATIONAL COVALENT MODIFICATION OF PROTEINS, B. C. Johnson, Ed., Academic Press, New York (1983), pgs. 1-12; Seifter, Meth. Enzymol. 182 (1990); 626-646, Rattan, Ann. NY Acad. Sci. 663 (1992); 48-62.

The polypeptide of the present invention has preferably the amino acid sequence encoded by a nucleic acid molecule of the present invention as described herein or is obtainable by a process for producing said polypeptide or by a process for producing cells capable of expressing said polypeptide which is described herein.

Preferably, in the context of the present invention the polypeptide is a bifunctional polypeptide. A "bifunctional polypeptide" means that the polypeptide of the present invention has, in addition to binding to methylated DNA, preferably to CpG methylated DNA, due to an Fc portion of an antibody which is part of the polypeptide of the present invention, further capabilities. For example, said Fc portion preferably offers the possibility to conjugate, link or covalently couple (a) compound(s) or moieties to said Fc portion. As used herein, the term "covalently coupled" means that the specified compounds or moieties are either directly covalently bonded to one another, or else are indirectly covalently joined to one another through an intervening moiety or moieties, such as a bridge, spacer, or linkage moiety or moieties.

Such (a) compound(s) may be a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to an Fc portion of an antibody (or fragment thereof) or indirectly, through an intermediate (such as, for example, a linker known in the art) using techniques known in the art. See, for example, U.S. Pat. No. 4,741,900 for metal ions which can be conjugated to an Fc portion of antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, or $^{99}$Tc.

Further, said Fc portion may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mereaptopurine, 6-thioguanine, cytarabine, 5-fluorouracil decarbazine), alkylating agents (e.g., mechlorethamine, thioepa chlormbucil, melphalan, carmustine (BSNU) and lomustine (CCNU), cyclothosphamide, busulfan, dibromomannitol, streptozotocin, mitomycin C, and cis-dichlorodiamine platinum (11) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Furthermore, the Fc portion of the polypeptide of the present invention may be coupled or conjugated to a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent.

The Fc portion also allows attachment of the polypeptide of the present invention to solid supports, which are particularly useful for immunoassays or purification of the target artigen as described herein. Such solid supports include, but are not limited to, glass, cellulose, polyacrylamide, nylon, polycabonate, polystyrene, polyvinyl chloride or polypropylene or the like.

Techniques for conjugating coupling or linked compounds to the Fc portion are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoelonal Antibodies For Cancer Detection And Therapy, Baldwin et al. (eds.), pp. 303-16 (Academic Press 1985), and Thorpe, Immunol. Rev., 119-158.

The term "DNA-binding domain of a protein belonging to the family of Methyl-CpG binding proteins (MBDs)" encompasses a polypeptide which has preferably the structural and/or functional characteristics of the methyl-DNA-binding domain of a protein of the MBD family which comprises the proteins MeCP2, MBD1, MBD2, MBD3 and MBD4. The methyl-DNA-binding activity can be tested by methods known in the art. Preferably, the term "methylated DNA" encompasses methylated DNA, more preferably, CpG methylated DNA including hemi-methylated or DNA methylated at both strands or single-stranded, methylated DNA. The most important example to date is methylated cytosine that occurs mostly in the context of the dinucleotide CpG, but also in the context of CpNpG- and CpNpN-sequences. In principle, other naturally occurring nucleotides may also be methylated.

It is preferred that the polypeptide of the present invention binds methylated DNA either as a monomer or dimer or multivalent molecule as described herein. It is preferably capable of binding to highly methylated DNA or low methylated DNA. Preferably, it can bind single methylated CpG pairs. MeCP2, MBD1, MBD2, MBD3 and MBD4 constitute a family of vertebrate proteins that share the methyl-CpG-binding domain. The MBD protein family comprises two subgroups based upon sequences of the known MBDs. The methyl-DNA-binding domain of MBD4 is most similar to that of MeCP2 in primary sequence, while the methyl-DNA-binding domain of MBD1, MBD2 and MBD3 are more similar to each other than to those of either MBD4 or MeCP2. However, the methyl-DNA-binding domains within each protein appear to be related evolutionarily based on the presence of an intron located at a conserved position within all five genes of MeCP2, MBD1, MBD2, MBD3 and MBD4. Yet, the sequence similarity between the members of the MBD family is largely limited to their methyl-DNA-binding domain, although MBD2 and MBD3 are similar and share about 70% of overall identity over most of their length. The greatest divergence occurs at the C-terminus, where MBD3 has 12 consecutive glutamic acid residues.

An MBD or fragment thereof preferably a methyl-DNA-binding domain or fragment thereof useful in accordance with the present invention can, for example, be identified by using sequence comparisons and/or alignments by employing means and methods known in the art, preferably those described herein and comparing and/or aligning (a) known MBD(s) to/with a sequence suspected to be an MBD.

For example, when a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The percentage identity between two sequences is a function of the number of matching or identical positions shared by the two sequences divided by the number of positions compared×100. For instance, if 6 of 10 of the positions in two sequences are matched or are identical, then the two sequences are 60% identical. By way of example, the DNA sequences CTGACT and CAGGTT share 50% homology (3 of the 6 total positions are matched). Generally, a comparison is made when two sequences are aligned to give maximum homology and/or identity. Such alignment can be provided using, for instance, the method of Needleman, J. Mol Biol. 48 (1970): 443-453, implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

Preferably, a methyl-DNA-binding domain or fragment thereof of the polypeptide of the present invention has the structural and/or functional characteristics as described herein. Preferably, a fragment of a methyl-DNA-binding protein described herein is able to bind methylated DNA, preferably CpG methylated DNA.

The methyl-DNA-binding domain or fragment thereof of the polypeptide of the present invention is preferably of insect origin, nematode origin, fish origin, amphibian origin, more preferably of vertebrate origin, even more preferably of mammal origin, most preferably of mouse and particularly preferred of human origin.

Preferably, the methyl-DNA-binding domain or fragment thereof of the polypeptide of the present invention possesses a unique alpha-helix/beta-strand sandwich structure with characteristic loops as is shown in FIG. 1 of Ballester and Wolffe, Eur. J. Biochem. 268 (2001), 1-6 and is able to bind methylated DNA.

More preferably, the MBD or fragment thereof of the polypeptide of the present invention comprises at least 50, more preferably at least 60, even more preferably at least 70 or at least 80 amino acid residues of the MBDs shown in FIG. 1 of Ballester and Wolffe (2001), loc. cit. and is able to bind methylated DNA.

Even more preferably, the methyl-DNA-binding domain or fragment thereof of the polypeptide of the present invention shares preferably 50%, 60%, 70%, 80% or 90%, more preferably 95% or 97%, even more preferably 98% and most preferably 99% identity on amino acid level to the MBDs shown in FIG. 1 of Ballester and Wolffe (2001), loc. cit. and is able to bind methylated DNA. Means and methods for determining the identity of sequences, for example, amino acid sequences is described elsewhere herein.

Most preferably, the methyl-DNA-binding domain or fragment thereof of the polypeptide of the present invention comprises the methyl-DNA-binding domain of the MBD proteins shown in FIG. 1 of Ballester and Wolffe (2001), loc. cit. or the methyl-DNA-binding domain of the MBD proteins described in Hendrich and Tweedy, Trends Genet. 19 (2003), 269-77 and is able to bind methylated DNA.

Of course, in accordance with the present invention, the polypeptide of the present invention is preferably bifunctional and harbours preferably two methyl-DNA-binding domains as described above, wherein preferably both methyl-DNA-binding domains are able to bind single methylated CpG pairs.

In a particular preferred embodiment of the invention, the methyl-DNA-binding domain of the polypeptide of the present invention is that of human MBD2. In a more particular preferred embodiment, the methyl-DNA-binding domain is that of human MBD2 comprising amino acids 144 to 230 of the amino acid sequence having Genbank accession number NM_003927. In a most particular preferred embodiment, the methyl-DNA-binding domain of the polypeptide of the present invention comprises the amino acid sequence from position 29 to 115 of the amino acid sequence shown in SEQ ID NO:2 (FIG. 1).

An "Fc portion" of an antibody which is a component of the polypeptide of the present invention comprises preferably at least a portion of the constant region of an immunoglobulin heavy chain molecule. The Fc region is preferably limited to the constant domain hinge region and the $C_H2$ and $C_H3$ domains. The Fc region in the polypeptide of the present invention can also be limited to a portion of the hinge region, the portion being capable of forming intermolecular disulfide bridges, and the $C_H2$ and $C_H3$ domains, or functional equivalents thereof.

Alternatively, it is also preferred that the Fc portion comprises at least so many $C_H$ regions which are required such that the polypeptide of the present invention has still the properties of the polypeptide described hereinabove, in particular the properties of the polypeptide used in the appended Examples.

In another alternative, it is also preferred that said constant region may contain one or more amino acid substitutions when compared to constant regions known in the art. Preferably it contains 1 to 100, 1 to 90, 1 to 80, 1 to 70, 1 to 60, 1 to 50, 1 to 40, 1 to 30 or 1 to 20, more preferably 1 to 10, even more preferably 1 to 9, 1 to 8, 1 to 7 or 1 to 6 and most preferably 1 to 5, 1 to 4, 1 to 3 or 2 or 1 substitution(s). The comparison is preferably done as is known in the art or, more preferably, as described elsewhere herein.

Alternatively, said constant region comprises preferably at least the $C_H1$ region, more preferably the $C_H1$ and $C_H2$ regions and most preferably the $C_H1$, $C_H2$ and $C_H3$ region. As is known in the art, the constant region of an antibody contains two immunoglobulin heavy chains which harbour three characteristic immunoglobulin domains composed of about 110 amino acids, wherein the two immunoglobulin heavy chains are covalently linked via disulfide bonds. Without being bound by theory, it is believed that the nascent polypeptide of the present invention comprising an methyl-DNA-binding domain and an Fc portion of an antibody is folded within a host cell such that preferably two polypeptides are joined at their Fc portion in a manner similar or, preferably, identical to the constant region of an antibody, resulting in a bifunctional polypeptide as described herein.

It is also envisaged that the constant region could preferably be of chicken or duck origin. Yet, preferably, the constant region is of the IgM, IgA, IgD or IgE isotype and more preferably it is of the IgG isotype, most preferably of the IgG1 isotype. Preferably, the aforementioned isotypes are of vertebrate origin, more preferably of mammal origin, even more preferably of mouse, rat, goat, horse, donkey, camel or chimpanzee origin and most preferably of human origin. Preferably, said IgG isotype is of class IgG1, IgG2, IgG3, IgG4 and said IgA isotype is of class IgA1, IgA2.

As described herein, the present invention provides preferably for bifunctional polypeptides. Yet, also multimeric bifunctional polypeptides comprising one or more of the bifunctional polypeptide of the present invention are envisaged. Such multimers may be generated by using those Fc regions, or portions thereof, of Ig molecules which are usually multivalent such as IgM pentamers or IgA dimers. It is understood that a J chain polypeptide may be needed to form and stabilize IgM pentamers and IgA dimers.

In a more preferred embodiment, the nucleic acid molecule comprising a nucleotide sequence of the present invention described hereinabove is selected from the group consisting of:
(a) a nucleic acid sequence having the nucleotide sequence shown in SEQ ID NO: 1 (FIG. 1);
(b) a nucleic acid sequence having a nucleotide sequence encoding a polypeptide having the amino acid sequence shown in SEQ ID: NO 2 (FIG. 1);

(c) a nucleic acid sequence having a nucleotide sequence encoding a fragment of a polypeptide having the amino acid sequence shown in SEQ ID: NO 2 (FIG. 1), wherein said fragment comprises at least amino acids 130 to 361 of said polypeptide and which is capable of binding methylated DNA;

(d) a nucleic acid sequence having a nucleotide sequence encoding a variant of a polypeptide encoded by a polynucleotide of any one of (a) to (c), wherein in said variant one or more amino acid residues are substituted compared to said polypeptide, and said variant is capable of binding methylated DNA;

(e) a nucleic acid sequence having a nucleotide sequence which hybridizes with a nucleic acid sequence of any one of (a) to (d) and which is at least 65% identical to the nucleotide sequence of the nucleic acid molecule of (a) and which encodes a polypeptide being capable of binding methylated DNA;

(f) a nucleic acid molecule encoding a polypeptide which is at least 65% identified to a polypeptide encoded by a nucleic acid molecule of (b) and which is capable of binding methylated DNA; and (g) a nucleic acid sequence having a nucleotide sequence being degenerate to the nucleotide sequence of the polynucleotide of any one of (a) to (f);

or the complementary strand of such a polynucleotide.

As described above, the fragment of the polypeptide of the present invention having the amino acid sequence shown in SEQ ID: NO 2 (FIG. 1) comprises at least amino acids 130 to 361 of the amino acid sequence shown in SEQ ID: NO 2 (FIG. 1). That means that said fragment may comprise in addition to amino acids 130 to 361 which represent the Fc portion, one or more amino acids such that said fragment is capable of binding methylated DNA, preferably, CpG methylated DNA, rather than unmethylated DNA. Accordingly, it is envisaged that said fragment comprises more preferably, at least amino acids 116 to 361 of the amino acid sequence shown in SEQ ID: NO 2 (FIG. 1). Even more preferably, said fragment may comprise at least amino acids 29 to 115 and 130 to 361 of the amino acid sequence shown in SEQ ID: NO 2 (FIG. 1). In a most preferred embodiment, said fragment may comprise at least amino acids 29 to 361. It is generally preferred that the fragments of the polypeptide of the present invention are able to bind to methylated DNA, preferably to CpG methylated DNA, rather than unmethylated DNA. This ability can be tested by methods known in the art or preferably by those methods described in the appended Examples.

A "variant" of the polypeptide of the present invention encompasses a polypeptide wherein one or more amino acid residues are substituted, preferably conservatively substituted compared to said polypeptide and wherein said variant is preferably able to bind to methylated DNA, preferably CpG methylated DNA. Such variants include deletions, insertions, inversions, repeats, and substitutions selected according to general rules known in the art so as have no effect on the activity of the polypeptide of the present invention. For example, guidance concerning how to make phenotypically silent amino acid substitutions is provided in Bowie, Science 247: (1990) 1306-1310, wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244: (1989) 1081-1085.) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al. above, such conservative substitutions are likely to be phenotypically silent. Additional guidance concerning which amino acid changes are likely to be phenotypically silent are found in Bowie, Science 247: (1990) 1306-1310.

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in the Table below.

TABLE IV

| For Amino Acid | Code | Replace with any of: |
|---|---|---|
| Alanine | A | D-Ala, Gly, beta-Ala, L-Cys, D-C$_3$s |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-As |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(0), L-Cys, D-Cys |

TABLE IV-continued

| For Amino Acid | Code | Replace with any of: |
|---|---|---|
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Infoliuaties and Genome Projects, Smith, D M., ed., Academic Press, New York, 1993; Informafies Computer Analysis of Sequence Data, Part 1, Griffin, A. M., and Griffin, H. G., eds., Humana Press, New Jersey, 1994; Sequence Analysis in Molecular Biology, von Heinje, G., Academie Press, 1987; and Sequence Analysis Primer, Gribskov, M. and Devereux, eds., M Stockton Press, New York, 1991.

As described above, the present invention preferably also relates to nucleic acid sequences which hybridize to the nucleic acid sequence shown in SEQ ID NO: 1 fragments or variants thereof as described herein (FIG. 1) and which are at least 65% identical to the nucleic acid sequence shown in SEQ ID NO: 1 (FIG. 1) and which preferably encode a polypeptide being capable of binding methylated DNA, preferably CpG methylated DNA, rather than unmethylated DNA. As also described, the present invention preferably relates to nucleic acid sequences encoding a polypeptide which is at least 65%, more preferably 70%, 75%, 80%, 85%, 90%, more preferably 99% identified to the polypeptide shown in SEQ ID NO:2. The term "hybridizes" as used in accordance with the present invention preferably relates to hybridizations under stringent conditions. The term "hybridizing sequences" preferably refers to sequences which display a sequence identity of at least 65%, even more preferably at least 70%, particularly preferred at least 80%, more particularly preferred at least 90%, even more particularly preferred at least 95% and most preferably at least 97, 98% or 99% identity with a nucleic acid sequence as described above encoding a polypeptide which is able to bind to methylated DNA, preferably CpG methylated DNA, rather than unmethylated DNA.

Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Such fragments may represent nucleic acid sequences as described herein. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., at least 65% identity, preferably, at least 70-95% identity, more preferably at least 95%, 96%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 65% to 95% or greater sequence identity are considered to be substantially identical. Such a definition also applies to the complement of a test sequence. Preferably the described identity exists over a region that is at least about 232 amino acids or 696 nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands.

For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum } BLAST \text{ score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

Moreover, the present invention also relates to nucleic acid molecules the sequence of which is degenerate in comparison with the sequence of an above-described nucleic acid molecules. When used in accordance with the present invention the term "being degenerate as a result of the genetic code" means that due to the redundancy of the genetic code different nucleotide sequences code for the same amino acid.

Of course, the present invention also envisages the complementary strand to the aforementioned and below mentioned nucleic acid molecules if they may be in a single-stranded form.

Preferably, the nucleic acid molecule according to the invention may be any type of nucleic acid, e.g. DNA, genomicDNA, cDNA, RNA or PNA (peptide nucleic acid).

For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The DNA may, for example, be genomic DNA or cDNA. The RNA may be, e.g., mRNA. The nucleic acid molecule may be natural, synthetic or semisynthetic or it may be a derivative, such as peptide nucleic acid (Nielsen, Science 254 (1991), 1497-1500) or phosphorothioates. Furthermore, the nucleic acid molecule may be a recombinantly produced chimeric nucleic acid molecule comprising any of the aforementioned nucleic acid molecules either alone or in combination.

Preferably, the nucleic acid molecule of the present invention is part of a vector. Therefore, the present invention relates in another embodiment to a vector comprising the nucleic acid molecule of this invention. Such a vector may be, e.g., a plasmid, cosmid, virus, bacteriophage or another vector used e.g. conventionally in genetic engineering, and may comprise further genes such as marker genes which allow for the selection and/or replication of said vector in a suitable host cell and under suitable conditions. In a preferred embodiment, said vector is an expression vector, in which the nucleic acid molecule of the present invention is operatively linked and to expression control sequence(s) allowing expression in prokaryotic or eukaryotic host cells as described herein. The term "operatively linked", as used in this context, refers to a linkage between one or more expression control sequences and the coding region in the polynucleotide to be expressed in such a way that expression is achieved under conditions compatible with the expression control sequence.

The nucleic acid molecules of the present invention may thus be inserted into several commercially available vectors. Nonlimiting examples include plasmid vectors compatible with mammalian cells, such as pUC, pBluescript (Stratagene), pET (Novagen), pREP (Invitrogen), pCRTopo (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRS- Vneo, pSV2-dhfr, pUCTag, pIZD35, pLXIN and pSIR (Clontech) and pIRES-EGFP (Clontech). Preferably, the nucleic acid molecules of the present invention are inserted into the vector Signal pIG plus (Ingenius, R&D Systems). Baculovirus vectors such as pBlueBac, BacPacz Baculovirus Expression System (CLONTECH), and MaxBac™ Baculovirus Expression System, insect cells and protocols (Invitrogen) are available commercially and may also be used to produce high yields of biologically active protein. (see also, Miller (1993), Curr. Op. Genet. Dev., 3, 9; O'Reilly, Baculovirus Expression Vectors: A Laboratory Manual, p. 127). In addition, prokaryotic vectors such as pcDNA2; and yeast vectors such as pYes2 are nonlimiting examples of other vectors suitable for use with the present invention.

Other preferred expression vectors of the present application are those for expressing proteins in *Drosophila* cells which are well known in the art, such as the DES®-series of Invitrogen. Preferably, said *Drosophila* cell expression vector is pMTBiP/V5-His B (Invitrogen). The pMT/BiP/V5-His vector offers the following additional features. It has a small size (3.6 kb) to improve DNA yields and increase subcloning efficiency, it has a C-terminal V5 epitope tag for rapid detection with Anti-V5 Antibody and it has a C-terminal 6×His tag for simple purification of recombinant fusion proteins using nickel-chelating resin.

For vector modification techniques, see Sambrook and Russel (2001), loc. cit. Vectors can contain one or more replication and inheritance systems for cloning or expression, one or more markers for selection in the host, e.g., antibiotic resistance, and one or more expression cassettes.

The coding sequences inserted in the vector can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Furthermore, the vectors may, in addition to the nucleic acid sequences of the invention, comprise expression control elements, allowing proper expression of the coding regions in suitable hosts. Such control elements are known to the artisan and may include a promoter, translation initiation codon, translation and insertion site or internal ribosomal entry sites (IRES) (Owens, Proc. Natl. Acad. Sci. USA 98 (2001), 1471-1476) for introducing an insert into the vector. Preferably, the nucleic acid molecule of the invention is operatively linked to said expression control sequences allowing expression in eukaryotic or prokaryotic cells.

Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor 1α-promoter, CMV enhancer, CaM-kinase promoter or SV40-enhancer.

For the expression in prokaryotic cells, a multitude of promoters including, for example, the tac-lac-promoter, the lacUV5 or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11.

An expression vector according to this invention is at least capable of directing the replication, and preferably the expression, of the nucleic acids and protein of this invention. Suitable origins of replication include, for example, the Col E1, the SV40 viral and the M 13 origins of replication. Suitable promoters include, for example, the cytomegalovirus (CMV) promoter, the lacZ promoter, the gallo promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like. Specifically-designed vectors allow the shuttling of DNA between different host cells, such as bacteria-yeast, or bacteria-animal cells, or bacteria-fungal cells, or bacteria invertebrate cells.

Beside the nucleic acid molecules of the present invention, the vector may further comprise nucleic acid sequences encoding for secretion signals. The secretion signal of the present invention that is preferably used in accordance with the present invention when the polypeptide of the present invention is expressed in *Drosophila* cells, preferably *Drosophila* S2 cells is the *Drosophila* BiP secretion signal well known in the art. The preferred BiP secretion signal that is used in the context of the present invention is shown in the amino acid sequence of SEQ ID NO: 2 at positions 1 to 28. Other secretion signal sequences are well known to the person skilled in the art. Furthermore, depending on the expression system used leader sequences capable of directing the expressed polypeptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof, into, inter alia, the extracellular membrane. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins of the invention may follow. Of course, the vector can also comprise regulatory regions from pathogenic organisms.

Furthermore, said vector may also be, besides an expression vector, a gene transfer and/or gene targeting vector. Gene therapy, which is based on introducing therapeutic genes (for example for vaccination) into cells by ex-vivo or in-vivo techniques is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957; Schaper, Current Opinion in Biotechnology 7 (1996), 635-640 or Verma, Nature 389 (1997), 239-242 and references cited therein.

The nucleic acid molecules of the invention and vectors as described herein above may be designed for direct introduction or for introduction via liposomes, or viral vectors (e.g. adenoviral, retroviral) into the cell. Additionally, baculoviral systems or systems based on vaccinia virus or Semliki Forest Virus can be used as eukaryotic expression system for the nucleic acid molecules of the invention. In addition to recombinant production, fragments of the protein, the fusion protein or antigenic fragments of the invention may be produced by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule.

The present invention in addition relates to a host cell genetically engineered with the nucleic acid molecule of the invention or a vector of the present invention. Said host may be produced by introducing said vector or nucleotide sequence into a host cell which upon its presence in the cell mediates the expression of a protein encoded by the nucleotide sequence of the invention or comprising a nucleotide sequence or a vector according to the invention wherein the nucleotide sequence and/or the encoded polypeptide is foreign to the host cell.

By "foreign" it is meant that the nucleotide sequence and/or the encoded polypeptide is either heterologous with respect to the host, this means derived from a cell or organism with a different genomic background, or is homologous with respect to the host but located in a different genomic environment than the naturally occurring counterpart of said nucleotide sequence. This means that, if the nucleotide sequence is homologous with respect to the host, it is not located in its natural location in the genome of said host, in particular it is surrounded by different genes. In this case the nucleotide sequence may be either under the control of its own promoter or under the control of a heterologous promoter. The location of the introduced nucleic acid molecule or the vector can be determined by the skilled person by using methods well-known to the person skilled in the art, e.g., Southern Blotting. The vector or nucleotide sequence according to the invention which is present in the host may either be integrated into the genome of the host or it may be maintained in some form extrachromosomally. In this respect, it is also to be understood that the nucleotide sequence of the invention can be used to restore or create a mutant gene via homologous recombination.

Said host may be any prokaryotic or eukaryotic cell. Suitable prokaryotic/bacterial cells are those generally used for cloning like *E. coli, Salmonella typhimurium, Serratia marcescens* or *Bacillus subtilis*. Said eukaryotic host may be a mammalian cell, an amphibian cell, a fish cell, an insect cell, a fungal cell, a plant cell or a bacterial cell (e.g., *E coli* strains HB101, DH5a, XL1 Blue, Y1090 and JM101). Eukaryotic recombinant host cells are preferred. Examples of eukaryotic host cells include, but are not limited to, yeast, e.g., *Saccharomyces cerevisiae, Schizosaccharomyces pombe, Kluyveromyces lactis* or *Pichia pastoris* cells, cell lines of human, bovine, porcine, monkey, and rodent origin, as well as insect cells, including but not limited to, *Spodoptera frugiperda* insect cells and zebra fish cells.

*Drosophila* cells, however, are preferred. More preferably, said *Drosophila* cells are *Drosophila* S2 (ATCC CRL-1963) which are, preferably used for heterologous protein expression in *Drosophila* expression systems, for example, the *Drosophila* Expression System (DES®). The S2 cell line was derived from a primary culture of late stage (20-24 hours old) *Drosophila melanogaster* embryos. This versatile cell line grows rapidly at room temperature without $CO_2$ and is easily adapted to suspension culture. Generally, when expressing the polypeptide of the present invention insect cells are preferred since they have the advantage that they contain less or, preferably no methylated DNA. Accordingly, when expressing and isolating and preferably purifying the polypeptide of the present invention, said polypeptide is preferably not contaminated with methylated DNA to which it can preferably bind. Another advantage of using insect cells is that they grow preferably in a protein-free medium which, thus, minimizes a further contamination of the polypeptide of the present invention when isolating, recovering and/or purifying the polypeptide of the present invention from preferably culture medium if said polypeptide is preferably secreted into said culture medium.

Mammalian species-derived cell lines suitable for use and commercially available include, but are not limited to, L cells, CV-1 cells, COS-1 cells (ATCC CRL 1650), COS-7 cells (ATCC CRL 1651), HeLa cells (ATCC CCL 2), C1271 (ATCC CRL 1616), BS-C-1 (ATCC CCL 26) and MRC-5 (ATCC CCL 171).

In another embodiment, the present invention relates to a method for producing a polypeptide which is capable of binding methylated DNA, preferably CpG methylated DNA comprising culturing the host cell of the invention and recovering the produced polypeptide. Said polypeptide is preferably encoded by a nucleic acid molecule of the invention. A preferred method for producing the polypeptide on the present invention is described in Example 2.

The present invention also provides a process for producing cells capable of expressing a polypeptide of the present invention which is capable of binding methylated DNA, preferably CpG methylated DNA comprising genetically engineering cells in vitro by methods known in the art or by those described herein. Said polypeptide is preferably encoded by a nucleic acid molecule of the present invention.

A large number of suitable methods exist in the art to produce polypeptides in appropriate hosts. If the host is a unicellular organism or a mammalian or insect cell, the person skilled in the art can revert to a variety of culture conditions that can be further optimized without an undue burden of work. Conveniently, the produced protein is harvested from the culture medium or from isolated (biological) membranes by established techniques. Furthermore, the produced polypeptide may be directly isolated from the host cell.

The polypeptide of the invention may be produced by microbiological methods or by transgenic mammals. It is also envisaged that the polypeptide of the invention is recovered from transgenic plants. Alternatively, the polypeptide of the invention may be produced synthetically or semi-synthetically.

For example, chemical synthesis, such as the solid phase procedure described by Houghton Proc. Natl. Acad. Sci. USA (82) (1985), 5131-5135, can be used. Another method is in vitro translation of mRNA. A preferred method involves the recombinant production of protein in host cells as described above. For example, nucleotide acid sequences comprising all or a portion of any one of the nucleotide sequences according to the invention can be synthesized by PCR, inserted into an expression vector, and a host cell transformed with the expression vector. Thereafter, the host cell is cultured to produce the desired polypeptide, which is isolated and purified. Protein isolation and purification can be achieved by any one of several known techniques; for example and without limitation, ion exchange chromatography, gel filtration chromatography and affinity chromatography, high pressure liquid chromatography (HPLC), reversed phase HPLC, preparative disc gel electrophoresis. In addition, cell-free translation systems can be used to produce the polypeptides of the present invention. Suitable cell-free expression systems for use in accordance with the present invention include rabbit reticulocyte lysate, wheat germ extract, canine pancreatic microsomal membranes, E. coli S30 extract, and coupled transcription/translation systems such as the TNT-system (Promega). These systems allow the expression of recombinant polypeptides or peptides upon the addition of cloning vectors, DNA fragments, or RNA sequences containing coding regions and appropriate promoter elements. As mentioned supra, protein isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein. After production of the polypeptide of the present invention it may be modified by pegylation, derivatization and the like.

In another embodiment the present invention relates to an antibody specifically binding to the polypeptide of the present invention. Preferably, the polypeptide has the cability to bind to methyled DNA and is a bifunctional protein as described herein.

The term "specifically" in this context means that the antibody reacts with the polypeptide of the present invention, but not with only portions of said polypeptide, e.g., with the methyl-DNA-binding domain, the Fc portion or a leader or secretion sequence. However, said antibody could specifically bind to the polypeptide linker of the polypeptide of the present invention if such a polypeptide linker is present.

Accordingly, said antibody binds specifically, for example, to a portion of the methyl-DNA-binding domain and the Fc portion of the polypeptide of the present invention or to a portion of the methyl-DNA-binding domain and the linker polypeptide or to a portion of the linker polypeptide and the Fc portionor as mentioned above, only to the linker polypeptide. Whether the antibody specifically reacts as defined herein above can easily be tested, inter alia, by comparing the binding reaction of said antibody with the portions as mentioned above and with only the respective portion(s) of the polypeptide of the present invention.

The antibody of the present invention can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", CSH Press, Cold Spring Harbor, 1988. These antibodies can be used, for example, for the immunoprecipitation and immunolocalization of the polypeptides of the invention as well as for the monitoring of the presence of such polypeptides, for example, in recombinant organisms or in diagnosis. They can also be used for the identification of compounds interacting with the proteins according to the invention (as mentioned herein below). For example, surface plasmon resonance as employed in the BIAcore system can be used to increase the efficiency of phage antibodies which bind to an epitope of the polypeptide of the invention (Schier, Human Antibodies Hybridomas 7 (1996), 97-105; Malmborg, J. Immunol. Methods 183 (1995), 7-13).

The present invention furthermore includes chimeric, single chain and humanized antibodies, as well as antibody fragments, like, inter alia, Fab fragments. Antibody fragments or derivatives further comprise F(ab')2, Fv or scFv fragments; see, for example, Harlow and Lane, loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies to polypeptide(s) of this invention. Also, transgenic animals may be used to express humanized antibodies to polypeptides of this invention. Most preferably, the antibody of this invention is a monoclonal antibody. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Techniques describing the production of single chain antibodies (e.g., U.S. Pat. No. 4,946,778) can be adapted to produce single chain antibodies to immunogenic polypeptides as described above. Furthermore, transgenic mice may be used to express humanized antibodies directed against said immunogenic polypeptides. It is in particular preferred that the antibodies/antibody constructs as well as antibody fragments or derivatives to be employed in accordance with this invention or capable to be expressed in a cell. This may, inter alia, be achieved by direct injection of the corresponding proteineous molecules or by injection of nucleic acid molecules encoding the same. Furthermore, gene therapy approaches are envisaged. Accordingly, in context of the present invention, the term "antibody molecule" relates to full immunoglobulin molecules as well as to parts of such immunoglobulin molecules. Furthermore, the term relates, as discussed above, to modified and/or altered antibody molecules, like chimeric and humanized antibodies. The term also relates to monoclonal or polyclonal antibodies as well as to recombinantly or synthetically generated/synthesized antibodies. The term also relates to intact antibodies as well as to antibody fragments thereof, like, separated light and heavy chains, Fab, Fab/c, Fv, Fab', F(ab')2. The term "antibody molecule" also comprises bifunctional antibodies and antibody constructs, like single chain Fvs (scFv) or antibody-fusion proteins. It is also envisaged in context of this invention that the term "antibody" comprises antibody constructs which may be expressed in cells, e.g. antibody constructs which may be transfected and/or transduced via, inter alia, viruses or vectors. Of course, the antibody of the present invention can be coupled, linked or conjugated to detectable substances as described herein above in connection with the Fc portion of the polypeptide of the present invention.

The present invention also provides a composition comprising the nucleic acid molecule, the vector, the host cell, the polypeptide or the antibody of the present invention.

The term "composition", as used in accordance with the present invention, relates to (a) composition(s) which comprise(s) at least one of the aforementioned compounds. It is envisaged that the compositions of the present invention which are described herein below comprise the aforementioned compounds in any combination. It may, optionally, comprise further molecules which are capable of binding methylated DNA, preferably CpG methylated DNA. The composition may be in solid, liquid or gaseous form and may be, inter alia, in the form of (a) powder(s), (a) tablet(s), (a) solution(s) (an) aerosol(s), granules, pills, suspensions, emulsions, capules, syrups, liquids, elixirs, extracts, tincture or fluid extracts or in a form which is particularly suitable for oral or parental or topic administration.

Additionally, the present invention relates to a kit comprising the nucleic acid molecule, the vector, the host, the polypeptide or the antibody of the present invention.

Advantageously, the kit of the present invention further comprises, optionally (a) reaction buffer(s), storage solutions and/or remaining reagents or materials required for the conduct of scientific or diagnostic assays or the like. Furthermore, parts of the kit of the invention can be packaged individually in vials or bottles or in combination in containers or multicontainer units.

The kit of the present invention may be advantageously used, inter alia, for carrying out the method for isolating, enriching, purifying and/or detecting methylated DNA as described herein and/or it could be employed in a variety of applications referred herein, e.g., as diagnostic kits, as research tools or therapeutic tools. Additionally, the kit of the invention may contain means for detection suitable for scientific, medical and/or diagnostic purposes. The manufacture of the kits follows preferably standard procedures which are known to the person skilled in the art.

As described above, the present invention is based on the surprising finding that a bifunctional, antibody-like molecule comprising a methyl-DNA-binding domain and an Fc portion of an antibody is able to specifically bind methylated DNA, preferably CpG methylated DNA with high affinity and high avidity which renders it a suitable diagnostic tool for isolating, enriching and/or detecting methylated DNA from more than 10 ng, less than 10 ng, less than 7.5 ng, less than 5 ng, less than 2.5 ng or from about 1 ng in a sample.

Accordingly, in a preferred embodiment the composition according to the invention is a diagnostic composition, optionally further comprising suitable means for detection.

A further embodiment of the present invention is the use of the polypeptide of the present invention for the detection of methylated DNA.

In addition, the nucleic acid molecules, the polypeptide, the vector, the host cell or the antibody of the present invention are used for the preparation of a diagnostic composition for detecting methylated DNA.

Moreover, the nucleic acid molecules, the polypeptide, the vector, the host cell or the antibody of the present invention are used for the preparation of a diagnostic composition for the detection of tumorous tissue or tumor cells.

As mentioned herein, the polypeptide of the present invention has unexpected superior properties, in particular for isolating, enriching, purifying and/or detecting methylated DNA, preferably CpG methylated DNA. Thus, the present invention provides various diagnostic uses and methods employing the polypeptide of the present invention. A preferred small scale enrichment procedure of methylated DNA, preferably CpG methylated DNA is described in Example 3. Briefly, the polypeptide of the present invention is, for example, bound to Protein A sepharose and washed to remove inbound protein. Next, DNA of interest is preferably digested and added to the bound polypeptide of the present invention. Furthermore, said digested DNA is incubated with the bound polypeptide of the present invention, washed and, after having been bound by the polypeptide of the present invention is eluted.

Accordingly, the present invention relates also to an in vitro method for detecting methylated DNA comprising
(a) contacting a sample comprising methylated and/or unmethylated DNA with the polypeptide of the present invention; and
(b) detecting the binding of said polypeptide to methylated DNA.

Preferably, said in vitro method is reverse South-Western blotting as exemplified in Example 3, immune precipitation, affinity purification of methylated DNA or Methyl-CpG-immunoprecipitation (MCIp) as exemplified in Example 4 and 5. However, said in vitro method is not limited thereto, but could basically be any procedure in which the polypeptide of the present invention is linked to a solid matrix, for example, a matrix such as sepharose, agarose, capillaries, vessel walls, as is also described herein in connection with the diagnostic composition of the present invention.

More preferably, the aforementioned in vitro methods further comprise as step (c) analyzing the methylated DNA, for example, by sequencing, Southern Blot, restriction enzyme digestion, bisulfite sequencing, pyrosequencing or PCR. Yet, analyzing methylated DNA which has been isolated, enriched, purified and/or detected by using the polypeptide of the present invention is not limited to the aforementioned methods, but encompasses all methods known in the art for analyzing methylated DNA, e.g. RDA, microarrays and the like.

Figure 7:
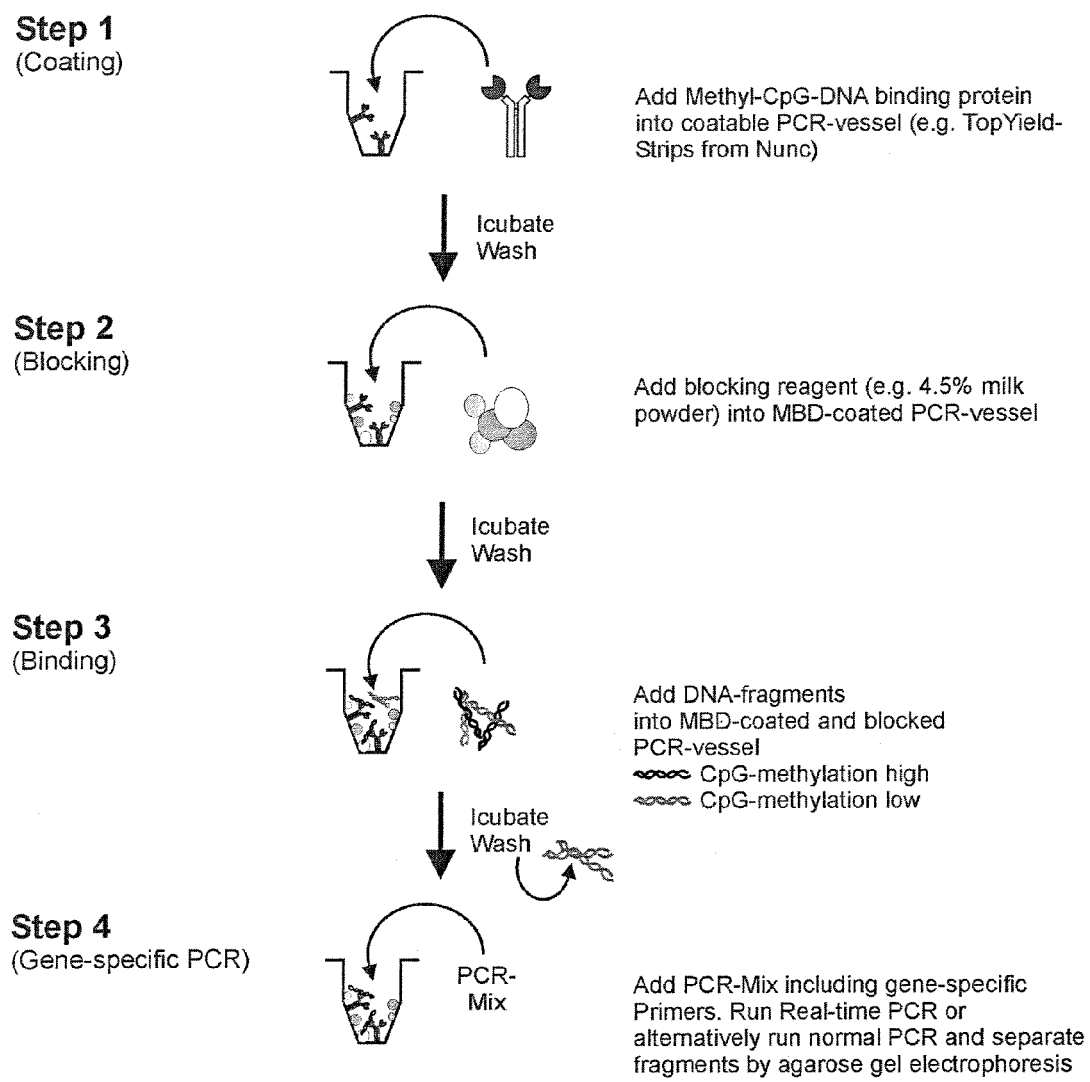

A preferred diagnostic application of the polypeptide of the present invention is the so-called MB-PCR shown in FIG. 7. Briefly, in a first step the polypeptide of the present invention is added into a coatable PCR-vessel, for example, TopYield Strips from Nunc. In doing so, the polypeptide is preferably coated onto the inner surface of said vessel by techniques known in the art. In a next step, blocking reagents, e.g., 4.5% milk powder is added into the coated PCR vessel. In a further step, preferably DNA-fragments of interest (for example, methylated and/or unmethylated DNA-fragments) are added into the coated and blocked PCR vessel. It is believed that the polypeptide of the present invention binds specifically to methylated DNA, if present. In a following step, the coated and blocked PCR vessel containing preferably DNA-fragments is incubated and then washed to remove unbound DNA-fragments. Afterwards, a PCR mix including preferably gene-specific primers or, but also preferred, at least two, three, four, five, six, seven etc. pairs of primers for, e.g., multiplex PCR for the gene or genlocus or genloci of interest which is/are suspected to be methylated or unmethylated is added to run preferably, a real time PCR or conventional PCR followed by gelelectrophoresis to separate amplification products.

MB-PCR is preferably done as follows:
Preferably, the PCR tubes are prepared using heat stable TopYield™ Strips (Nunc Cat. No. 248909). Preferably, 50 µl of the polypeptide of the present invention, preferably, in a recombinant form (diluted at 15 µg/ml in 10 mM Tris/HCl pH 7.5) were added to each well and incubated overnight at 4° C. Preferably, wells are washed three times with 200 µl TBS (20 mM Tris, pH 7.4 containing 150 mM NaCl) and blocked overnight at 4 C with 100 µl Blocking Solution (10 mM Tris, pH 7.5 containing 150 mM NaCl, 4.5% skim milk powder, 5 mM EDTA and 0.8 µg/ml of each poly d(I/C), poly d(A/T) and poly d(CG)). Preferably, tubes are then washed three times with 200 µl TBST (TBS containing 0.1% Tween-20).

Preferably, 50 µl Binding Buffer (20 mM Tris, pH 7.5 containing 400 mM NaCl, 2 mM MgCl$_2$, 0.5 mM EDTA, and 0.1% Tween-20) are added to each well and preferably 1 µl of digested DNA, preferably genomic DNA digested with MseI in an amount of preferably 10 ng/µl is added to every second well (M-reaction).

Genomic DNA is preferably prepared by using a kit known in the art, for example, using Blood and Cell Culture Midi Kit (Qiagen). The quality of the genomic DNA-preparation is preferably controlled by agarose gel electrophoresis and DNA concentration was preferably determined by UV spectrophotometry. Quantitation of DNA is preferably done by using PicoGreen dsDNA Quantitation Reagent (Molecular Probes).

The wells containing the polypeptide of the present invention and DNA, preferably DNA-fragments (generated by enzymatic digestion or mechanically fragmented) are incubated on a shaker at preferably 4° C. for preferably 3 hours. Preferably, tubes were washed three times with 200 µl Binding Buffer and once with 10 mM Tris/HCl pH 7.5.

Next, PCR was preferably carried out directly in the TopYield™ Strips. Preferably, the PCR-Mix (50 µl/well) contained a standard PCR buffer (Roche), preferably 2.5 U Fast-Start Taq DNA Polymerase (Roche), preferably 10 µmol of each gene-specific primer (synthesized by Qiagen), dNTPs (preferably 200 mM each, Amersham/Pharmacia) preferably 1 M betaine (Sigma), primer sequences and cycling parameters for specific genes of interest are shown in Tables 2 and 3 in Example 6. Of course, any other suitable gene specific or genlocus specific or genloci specific primers can be designed by the person skilled in the art. Moreover, the skilled artisan can readily determine and/or test the PCR parameters most suitable for the primer(s) and gene(s), genlocus/genloci of interest. After adding the PCR-mix, preferably 1 µl Mse I-digested DNA (preferably in an amount of 10 ng/µl) is added to every second other well, that was not previously incubated with DNA-fragments (P-reaction). Preferably, PCR-products are analysed using agarose gel electrophoresis and the ethidium bromide stained gel was scanned using, for example, a Typhoon 9200 Imager (Amersham/Pharmacia).

Accordingly, it is envisaged that the polypeptide of the present invention is useful for the detection of methylated DNA, preferably CpG-methylated DNA in a sample as described herein below which may include (a) single cell(s). It is also envisaged to be useful for whole cells. "Whole cell" means the genomic context of a whole single cell. Thus, it could be useful for a genome-wide analysis of methylated DNA.

Such a method comprises preferably an enriching/purifying step of methylated DNA using the polypeptide of the present invention and a detection step, e.g., hybridization of genomic DNA microarrays, tiling arrays, low-density arrays or lab-on-a-chip-approaches. The person skilled in the art is readily in a position to carry out the detection methods which are known in the art. Some of them are shown in the appended Examples, wherein the polypeptide of the present invention is used for enriching, purifying and/or isolating methylated DNA. One Example shows a so-called MB-PCR which may be suitable for high-throughput, robust one-tube assays. Furthermore, the polypeptide of the present invention may be particularly useful in the detection of CpG-methylation on single gene level. Such a method preferably comprises the step of enriching and/or purifying methylated DNA, preferably CpG-methylated DNA of a single gene and the step of detecting said methylated DNA by employing PCR, real-time PCR and the like.

Another possible diagnostic application of the polypeptide of the present invention is immunohistochemistry. Accordingly, the polypeptide of the present invention can be used to "stain" methylated DNA, preferably CpG-methylated DNA. Either the polypeptide of the present invention is via its Fc portion coupled, linked or conjugated to a suitable detectable substance as described herein or, for example, a second anti-Fc portion antibody is used for detecting the polypeptide of the present invention when bound to methylated DNA.

It is assumed that some malignancies can be detected by the methods of the present invention by their methylation pattern/profile which may, thus, be of a prognostic and/or predicable value. That means that the methylation pattern can be used for setting up a pharmacologic profile for a patient. For example, the susceptibility and/or sensitivity to, e.g., anti-cancer drug may be determined if it is detected that certain oncogenes and/or tumor suppressor genes are either hyper- or hypomethylated. Accordingly, the skilled artisan chooses the most appropriate medicament to avoid negative and/or adverse effects if, for example, said medicament may inhibit oncogenes although said oncogenes are already hypermethylated and, thus, assumed to be inactive.

The herein described methods may be useful for, firstly, identifying genloic and/or genes which are hyper- or mypomethylated in a malignancy such as cancer or a tumorous disease and, secondly, provide the basis for assaying the methylation status of such genloci and/or genes on a single gene level. Said malignancies are preferably tumors The tumor can any possible type of tumor. Examples are skin, breast, brain, cervical carcinomas, testicular carcinomas, head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukaemia, a paraneoplastic syndrome, a peritoneal carcinomastosis, a immunosuppression-related malignancy and/or metastatic cancer etc. The tumor cells may, e.g., be derived from: head and neck, comprising tumors of the nasal cavity, paranasal sinuses, nasopharynx, oral cavity, oropharynx, larynx, hypopharynx, salivary glands and paragangliomas, a cancer of the lung, comprising non-small cell lung cancer, small cell lung cancer, a cancer of the mediastinum, a cancer of the gastrointestinal tract, comprising cancer of the oesophagus, stomach, pancreas, liver, biliary tree, small intestine, colon, rectum and anal region, a cancer of the genitourinary system, comprising cancer of the kidney, urethra, bladder, prostate, urethra, penis and testis, a gynaecologic cancer, comprising cancer of the cervix, vagina, vulva, uterine body, gestational trophoblastic diseases, ovarian, fallopian tube, peritoneal, a cancer of the breast, a cancer of the endocrine system, comprising a tumor of the thyroid, parathyroid, adrenal cortex, pancreatic endocrine tumors, carcinoid tumor and carcinoid syndrome, multiple endocrine neoplasias, a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatosis, neuroblastoma, Ewing's sarcoma family of tumors, rhabdomyosarcoma, a lymphoma, comprising non-Hodgkin's lymphomas, cutaneous T-cell lymphomas, primary central nervous system lymphoma, and Hodgkin's disease, a leukaemia, comprising acute leukemias, chronic myelogenous and lymphocytic leukemias, plasma cell neoplasms and myelodysplastic syndromes, a paraneoplastic syndrome, a cancer of unknown primary site, a peritoneal carcinomastosis, a immunosuppression-related malignancy, comprising AIDS-related malignancies, comprising Kaposi's sarcoma, AIDS-associated lymphomas, AIDS-associated primary central nervous system lymphoma, AIDS-associated Hodgkin's disease and AIDS-associated anogenital cancers, and transplantation-related malignancies, a metastatic cancer to the liver, metastatic cancer to the bone, malignant pleural and pericardial effusions and malignant ascites. It is mostly preferred that said cancer or tumorous disease is cancer of the head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukemia, a paraneoplastic syndrome, a peritoneal carcinomastosis, a immunosuppression-related malignancy and/or metastatic cancer. Preferred tumors are AML, plasmacytoma or CLL.

The diagnostic composition of the present invention comprises at least one of the herein described compounds of the invention. The diagnostic composition may be used, inter alia, for methods for isolating, enriching and/or determining the presence of methylated DNA, preferably CpG methylated DNA, for example, in a sample from an individual as described above.

In accordance with the present invention by the term "sample" is intended any biological sample obtained from an individual, cell line, tissue culture, or other source containing polynucleotides or polypeptides or portions thereof. As indicated, biological samples include body fluids (such as blood, sera, plasma, urine, synovial fluid and spinal fluid) and tissue sources found to express the polynucleotides of the present invention. Methods for obtaining tissue biopsies and body fluids from mammals are well known in the art. A biological sample which includes genomic DNA, mRNA or proteins is preferred as a source.

Further applications of the diagnostic compositions are described herein and are shown in the appended Examples.

The diagnostic composition optionally comprises suitable means for detection. The nucleic acid molecule(s), vector(s), host(s), antibody(ies), and polypeptide(s) described above are, for example, suitable for use in immunoassays in which they can be utilized in liquid phase or bound to a solid phase carrier. Examples of well-known carriers include glass, polystyrene, polyvinyl ion, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention.

Solid phase carriers are known to those in the art and may comprise polystyrene beads, latex beads, magnetic beads, colloid metal particles, glass and/or silicon chips and surfaces, nitrocellulose strips, membranes, sheets, duracytes and the walls of wells of a reaction tray, plastic tubes or other test tubes. Suitable methods of immobilizing nucleic acid molecule(s), vector(s), host(s), antibody(ies), aptamer(s), polypeptide(s), etc. on solid phases include but are not limited to ionic, hydrophobic, covalent interactions or (chemical) crosslinking and the like. Examples of immunoassays which can utilize said compounds of the invention are competitive and non-competitive immunoassays in either a direct or indirect format. Commonly used detection assays can comprise radioisotopic or non-radioisotopic methods. Examples of such immunoassays are the radioimmunoassay (RIA), the sandwich (immunometric assay) and the Northern or Southern blot assay. Furthermore, these detection methods comprise, inter alia, IRMA (Immune Radioimmunometric Assay), EIA (Enzyme Immuno Assay), ELISA (Enzyme Linked Immuno Assay), FIA (Fluorescent Immuno Assay), and CLIA (Chemioluminescent Immune Assay). Furthermore, the diagnostic compounds of the present invention may be are employed in techniques like FRET (Fluorescence Resonance Energy Transfer) assays.

Appropriate labels and methods for labeling are known to those of ordinary skill in the art. Examples of the types of labels which can be used in the present invention include inter alia, fluorochromes (like fluorescein, rhodamine, Texas Red, etc.), enzymes (like horse radish peroxidase, β-galactosidase, alkaline phosphatase), radioactive isotopes (like $^{32}P$, $^{33}P$, $^{35}S$ or $^{125}I$), biotin, digoxygenin, colloidal metals, chemi- or bioluminescent compounds (like dioxetanes, luminol or acridiniums).

A variety of techniques are available for labeling biomolecules, are well known to the person skilled in the art and are considered to be within the scope of the present invention and comprise, inter alia, covalent coupling of enzymes or biotinyl groups, phosphorylations, biotinylations, random priming, nick-translations, tailing (using terminal transferases). Such techniques are, e.g., described in Tijssen, "Practice and theory of enzyme immunoassays", Burden and von Knippenburg (Eds), Volume 15 (1985); "Basic methods in molecular biology", Davis L G, Dibmer M D, Battey Elsevier (1990); Mayer, (Eds) "Immunochemical methods in cell and molecular biology" Academic Press, London (1987); or in the series "Methods in Enzymology", Academic Press, Inc. Detection methods comprise, but are not limited to, autoradiography, fluorescence microscopy, direct and indirect enzymatic reactions, etc.

Another preferred composition of the present invention is a pharmaceutical composition optionally further comprising a pharmaceutical acceptable carrier. Said pharmaceutical composition comprises, inter alia, the polypeptide of the present invention which may be coupled to a further polypeptide, for example, a histone deacetylase, a histone acetylase, DNA-methylase and/or DNA-demethylase. It could also be coupled with a restriction enzyme or a ribozyme. It is believed that if the polypeptide of the present invention coupled with one or more further proteian as described above binds to methylated DNA, it may target said further protein(s) to DNA. Accordingly, a DNA-methylase could hyper-methylate a hypomethylated DNA, for example, a hypomethylated oncogenic locus or oncogene or a DNA. In doing so, gene inactivation could be achieved.

Alternatively, a DNA-demethylase may demethylate a hypermethylated gene or genlocus, for example, a tumor suppressor gene or genlocus. In doing so, gene activation could be achieved.

A histone deacetylase contribute to transcriptional repression of an active gene by deacetylating acetylated lysine residues of histones, thereby leading to a tighter packaging of DNA to histones and, gene repression. A histone acetylase could do the contrary effect as is known in the art.

A restriction enzyme or a ribozyme could exert its effect when targeted to DNA which should be cleaved. Appropriate restriction enzymes are known in the art. Ribozymes specific for target-DNA sequences can be prepared as is known in the art.

Accordingly, the pharmaceutical composition could be useful for treating cancer and/or tumorous disease. Both of which are known to be caused by uncontrolled gene expression, activation and/or repression which is, inter alia, regulated by histone acetylation/deacetylation and/or DNA-methylation/demethylation.

The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like.

Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the aforementioned compounds, preferably in purified form, together with a suitable amount of carrier so as to provide the form for proper administration to the patient. The formulation should suit the mode of administration.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The pharmaceutical composition is preferably designed for the application in gene therapy. The technique of gene therapy has already been described above in connection with the nucleic acid molecules of the invention and all what has been said there also applies in connection with the pharmaceutical composition. For example, the nucleic acid molecule in the pharmaceutical composition is preferably in a form which allows its introduction, expression and/or stable integration into cells of an individual to be treated.

For gene therapy, various viral vectors which can be utilized, for example, adenovirus, herpes virus, vaccinia, or, preferably, an RNA virus such as a retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can also incorporate multiple genes. All of these vectors can transfer or incorporate a gene for a selectable marker so that transduced cells can be identified and generated. Retroviral vectors can be made target specific by inserting, for example, a polynucleotide encoding a sugar, a glycolipid, or a protein. Those of skill in the art will know of, or can readily ascertain without undue experimentation, specific polynucleotide sequences which can be inserted into the retroviral genome to allow target specific delivery of the retroviral vector containing the inserted polynucleotide sequence.

Since recombinant retroviruses are preferably defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to w2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium. Another targeted delivery system for the nucleic acid molecules of the present invention is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 pm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries.

In a preferred embodiment, the compositions of the present invention may be useful for in vivo imaging methylated DNA, preferably CpG methylated DNA. Accordingly said composition is administered to a subject in need thereof. In the context of the present invention the term "subject" means an individual in need of a treatment of an affective disorder. Preferably, the subject is a vertebrate, even more preferred a mammal, particularly preferred a human. The term "administered" means administration of a therapeutically or diagnostically effective dose of the aforementioned nucleic acid molecule encoding the polypeptide of the present invention to an individual. By "therapeutically or diagnostically effective amount" is meant a dose that produces the effects for which it is administered. The exact dose will depend on the purpose of the treatment or diagnosis, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art. The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents maybe administered alone or in combination with other treatments.

The administration of the pharmaceutical composition can be done in a variety of ways as discussed above, including, but not limited to, orally, subcutaneously, intravenously, intra-arterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly. In some instances, for example, in the treatment of wounds and inflammation, the candidate agents may be directly applied as a solution dry spray.

The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition. Dosages will vary but a preferred dosage for intravenous administration of DNA is from approximately $10^6$ to $10^{12}$ copies of the DNA molecule. If the regimen is a continuous infusion, it should also be in the range of 1 µg to 10 mg units per kilogram of body weight per minute, respectively. Progress can be monitored by periodic assessment. The pharmaceutical composition of the invention may be administered locally or systemically. Administration will preferably be parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium ion solution, Ringer's dextrose, dextrose and sodium ion, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

It is also envisaged that the pharmaceutical compositions are employed in co-therapy approaches with other agents, for example, useful in detecting methylated DNA and, thus, for example, useful in diagnosing malignancies which may show a typical methylated pattern.

The figures show:

FIG 1: FIG. 1 shows the nucleotide sequence of plasmid pMTBip/MBD2-Fc (SEQ ID NO:1) and the protein sequence (in bold; see also SEQ ID NO:2) of the MBD2-Fc bifunctional protein which is encoded by plasmid pMTBip/MBD2-Fc.

The amino acid sequence of the MBD2-Fc bifunctional protein has the following features.

AA 1-28 (nt 851-934): Drosophila BiP secretion signal (leader peptide from pMT/BipV5-His vector)
AA 29-115 (nt 935-1196): AA 144-230 of human MBD2
AA 116-129 (nt 1196-1237): Flexible Linker (amino acids 116-129 of SEQ ID NO:2)
AA 130-36 (nt 2381933): AA,99-330 of human IGHG1

FIG. 2: Expression of MBD2-$F_c$ in *Drosophila* Schneider-cells. Stably transfected S2 cells were seeded in Medium w/o FCS, with and w/o 500 µM CuSO$_4$. The supernatant was collected after 4 days and precleared o/n at 4° C. using sepharose beads. 1 ml precleared supernatant was precipitated using protein A sepharose, washed, resuspended in SDS-loading dye and subjected to SDS-PAGE. The gel was Coomassie-stained to detect precipitated protein.

Figure 3:
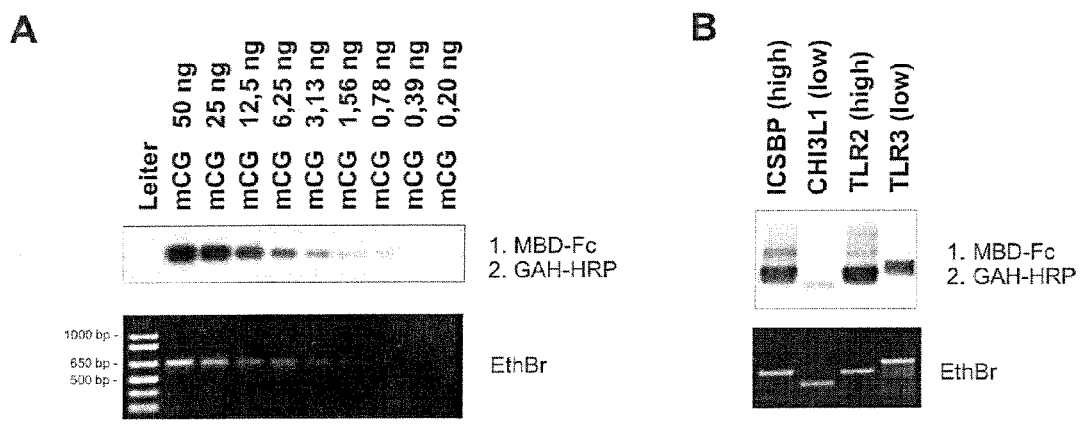

FIG. 3: Reverse South-Western Blot. A 650 by PCR-fragment of human ICSBP-promoter (A) or methylated promoter fragments (50 ng) of varying CpG-density (B)(number of CpG-dinucleotides/100 bp: ICSBP: 10,6; CHI3L1: 2,9; TLR2: 6,2; TLR3: 2,1) were methylated using SssI, subjected to agarose gel electrophoresis (ethidium bromide staining is shown as control) and directly blotted onto nylon membrane. Membranes were stained using MBD2-Fc, HRP-conjugated anti-human Fc and ECL as described in Example 3.

Figure 4:
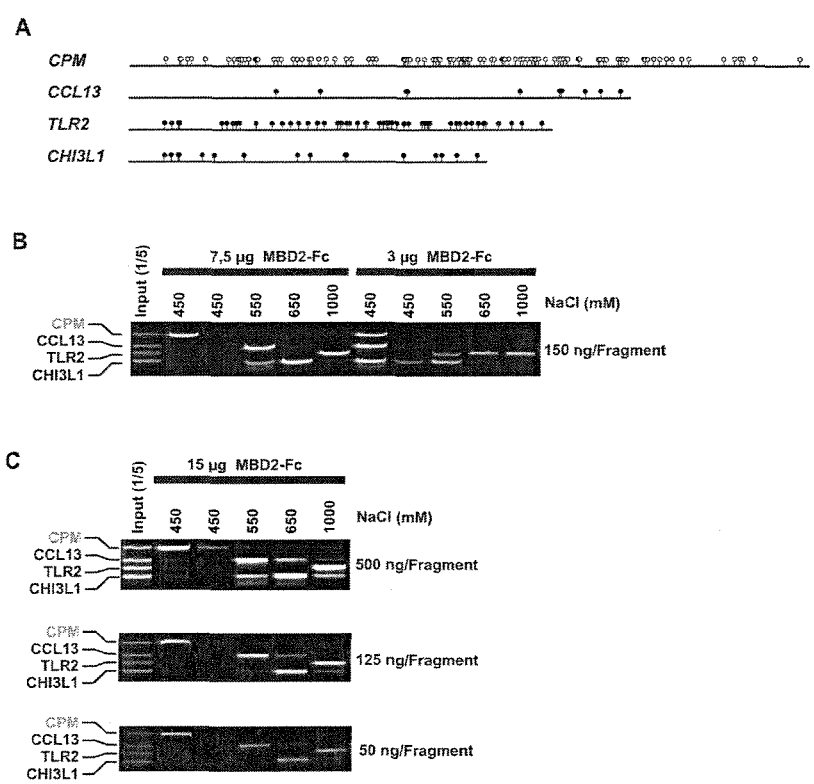

FIG. 4: Salt concentration-dependent binding of CpG-methylated to MBD-Fc beads (A) Schematic presentation of human promoter fragments. Circles mark the position of CpG-dinucleotides (○: unmethylated—CPM; ●SssI methylated—CCL13, TLR2, CHI3L1). (B, C) A mixture of methylated and un-methylated fragments were bound to MBD2-Fc-sepharose (amount of MBD2-Fc/50 µl protein A-sepharose is given) eluted using increasing salt concentrations, purified and separated using agarose gel electrophoresis (along with ⅕ of the Input mixture). Bands were visualised with ethidium bromide and scanned using a Typhoon Imager (Pharmacia-Amersham).

Figure 5:
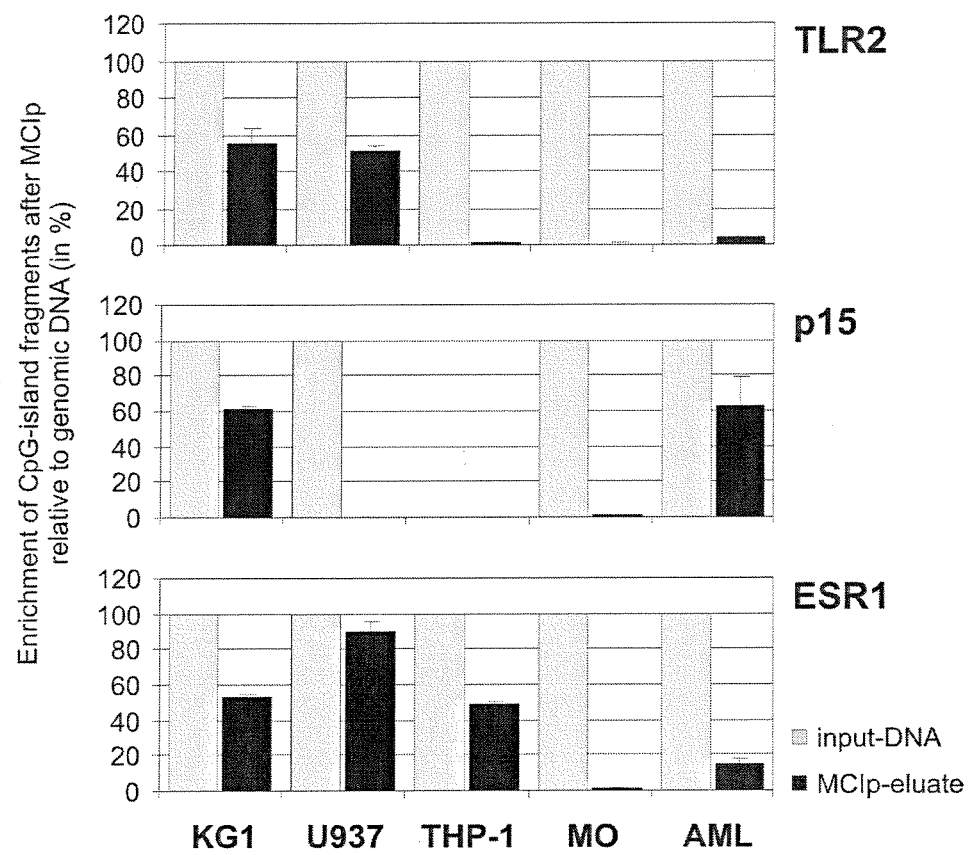

FIG. 5: Enrichment of CpG-islands by MCIp. Genomic DNA (300 ng) of the indicated cell types was subjected to MCIp. The enrichment of three CpG island promoters (TLR2, p15 and ESR1) was quantified using LightCycler real-time PCR. The amount of a particular promoter fragment amplified from the MCIp-eluate is shown relative to the untreated genomic DNA-control. The p15 promoter was undetectable in THP-1 cells indicating a mutation or deletion of this gene.

Figure 6:
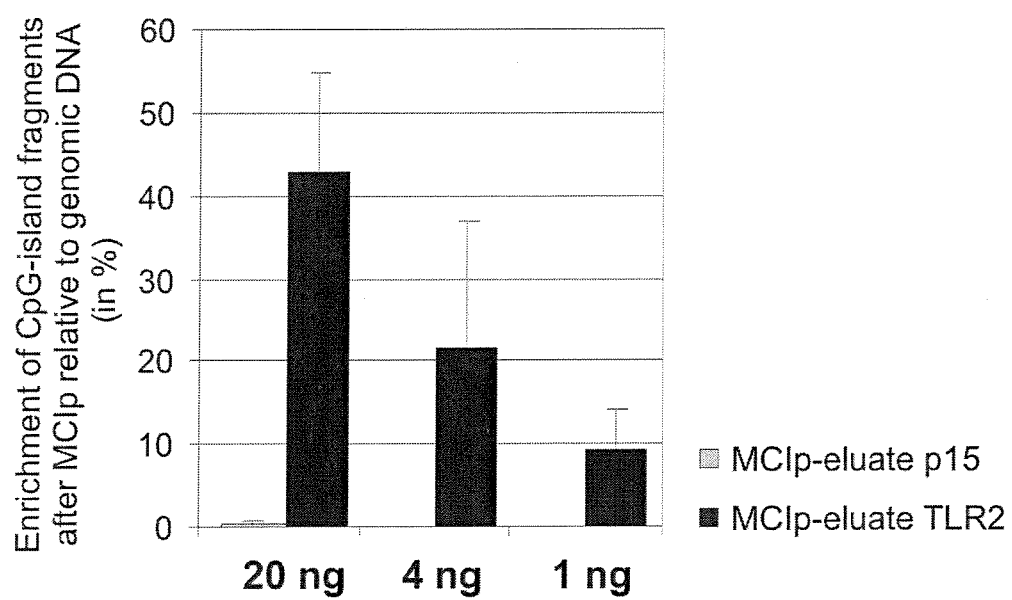

FIG. 6: Sensitivity of methylated CpG-island detection by MCIp. Decreasing amounts of restricted genomic U937 DNA was subjected to MCIp. The enrichment of the two CpG island promoters (TLR2, p15) was quantified using LightCycler real-time PCR. The amount of a particular promoter fragment amplified from the MCIp-eluate is shown relative to the untreated genomic DNA-control.

FIG. 7: Principle of MB-PCR. This figure shows a schematic representation of MB-PCR.

Figure 8:
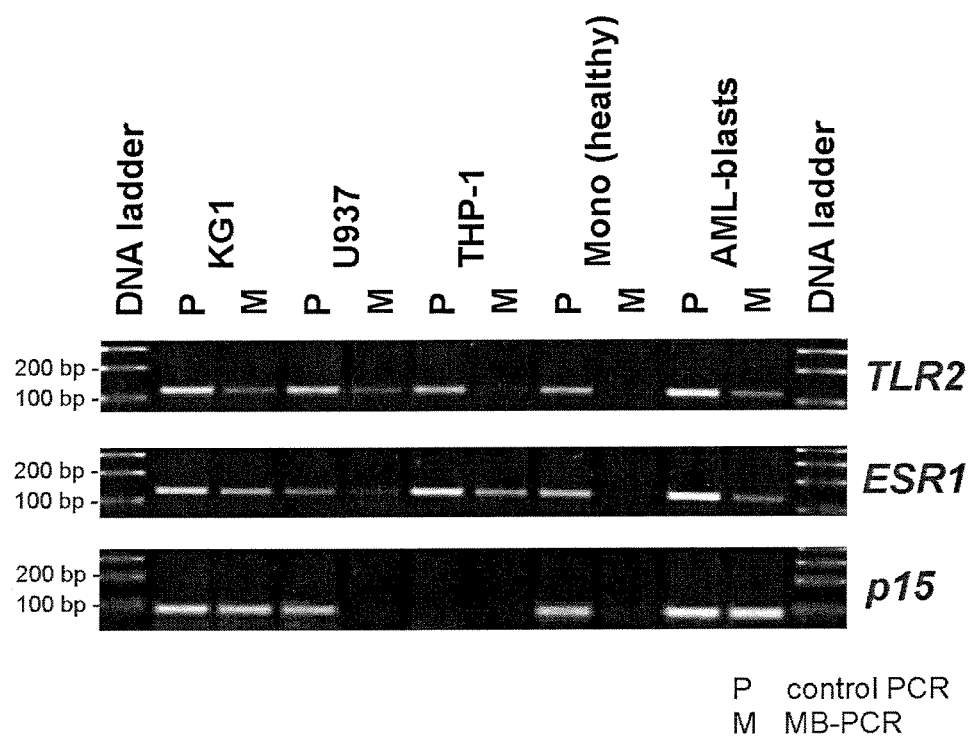

FIG. 8: MB-PCR of TLR2, ESR1 and p15 promoters in a normal and four leukemic DNA samples. Genomic DNA (10 ng) of the indicated cell types was subjected to MB-PCR. The enrichment of three CpG island promoters (TLR2, p15 and ESR1) was detected by standard genomic PCR. The p15 promoter was undetectable in THP-1 cells indicating a mutation or deletion of this gene.

Figure 9:
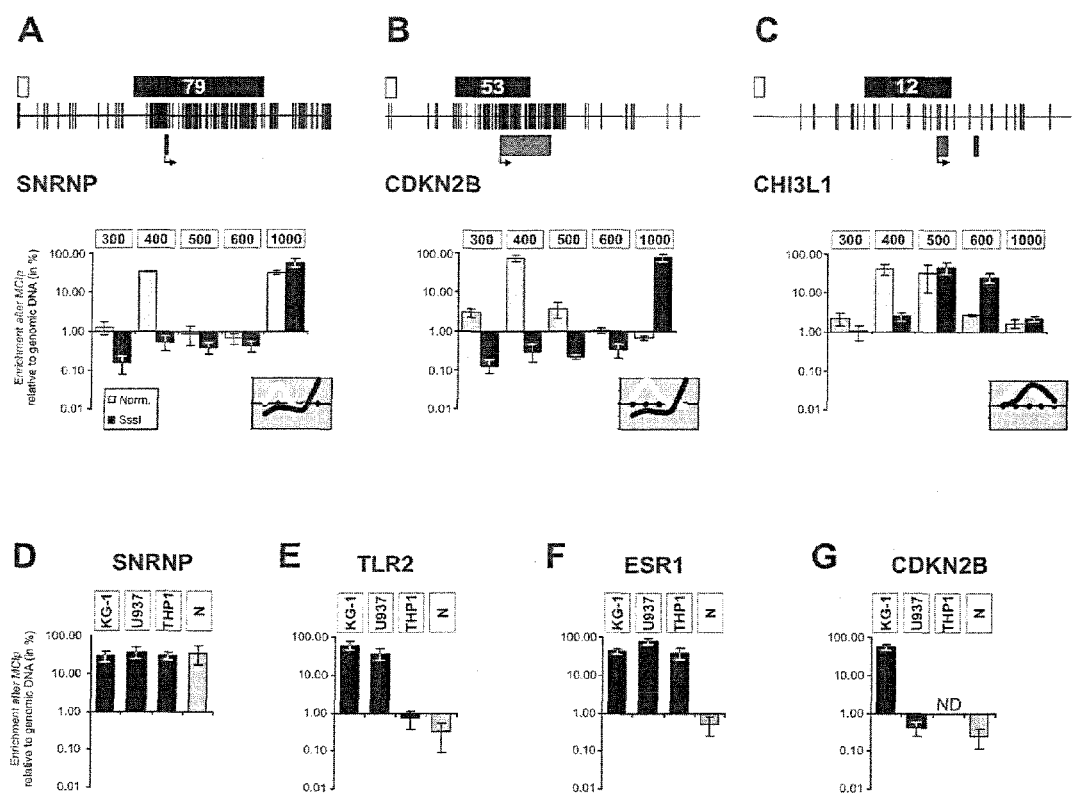

FIG. 9: MCIp detection of CpG methylation in specific CpG island promoters using real-time PCR. (A-C) Fractionated Methyl-CpG immunoprecipitation (MCIp) was used in combination with real-time LightCycler PCR to detect the methylation status of the indicated genes from untreated (gray bars) and SssI-methylated and MseI-restricted genomic DNA fragments (black bars). Recovered gene fragments from MCIp-eluates (NaCl-concentrations (in mM) are given in boxes above) and an equivalent amount of input-DNA were amplified by LightCycler-PCR. Values (mean±SD, n=4) of individual fractions represent the percentage of recovery and are calculated relative to the amount of PCR-product generated from the respective input-DNA (100%). Above each figure a 3 kB region of the corresponding CpG island is schematically presented. Each CpG dinucleotide is represented by a vertical line. The positions of exons are indicated as grey boxes and transcription start sites by an arrow. The white box represents a 100 bp fragment. Black boxes indicate the positions of the MseI-fragments that are detected. (D-G) SNRPN, TLR2, ESR1 and CDKN2B gene fragments in the high salt (1000 mM) MCIp fraction of three human myeloid leukaemia cell lines (KG-1, U937 and THP-1) as well as normal human blood monocytes (N) were analysed by Real time PCR as above.

Figure 10:
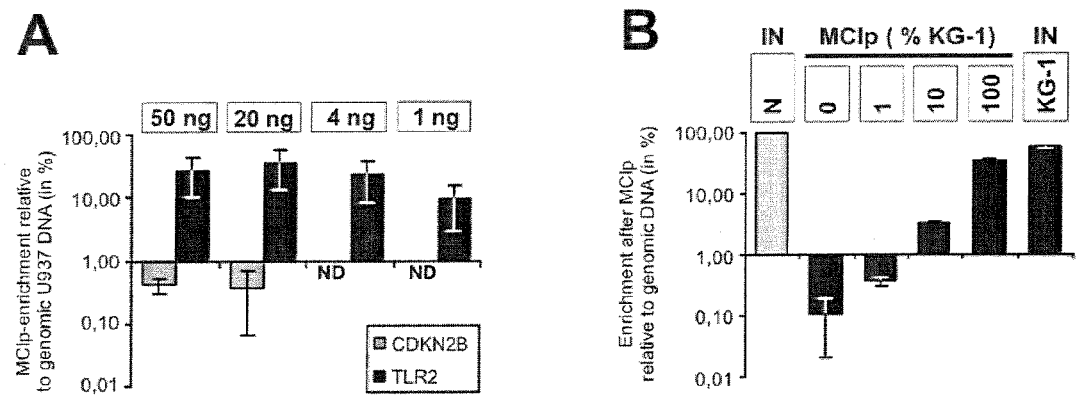

FIG. 10: Sensitivity and linearity of the MCIp approach. (A) Decreasing amounts of MseI-treated U937 DNA were subjected to MCIp. CDKN2B and TLR2 gene fragments were quantified as above. (B). MseI-treated DNA of normal human blood monocytes (N) and KG-1 cells was mixed at the indicated ratios and the mixture was subjected to MCIp and the TLR2 gene fragment was quantified using LightCycler-PCR as above.

A better understanding of the present invention and of its many advantages will be seen from the following examples, offered for illustrative purposes only, and are not intended to limit the scope of the present invention in any way.

EXAMPLE 1

Cloning of pMTBip/MBD2-Fc

A cDNA corresponding to the methyl-CpG binding domain (MBD) of human MBD2 (Genbank acc. no. NM_003927; AA 144-230) was PCR-amplified from reverse transcribed human primary macrophage total RNA using primers MBD2-Nhe_S (5'-AGA TGC TAG CAC GGA GAG CGG GAA GAG G-3') (SEQ ID NO: 4) and MBD2-Not_AS (5'-ATC ACG CGG CCG CCA GAG GAT CGT TTC GCA GTC TC-3') (SEQ ID NO: 5) and Herculase DNA Polymerase (Stratagene). Cycling parameters were: 95° C., 3 min denaturation; 95° C., 20 s, 65° C., 20 s, 72° C., 80 s amplification for 34 cycles; 72° C., 5 min final extension. The PCR-product was precipitated, digested with Not I/Nhe I, cloned into NotI/NheI-sites of Signal pIg plus vector (Ingenius, R&D Systems) and sequence verified resulting in pIg/MBD2-Fc (eucaryotic expression vector). To clone pMTBip/MBD2-Fc for recombinant expression in Drosophila S2 cells, the Apa I/Nhe I-fragment of pIg/MBD2-Fc containing the MBD of human MBD2 fused to the Fc-tail of human IgG1 was subcloned into Apa I/Spe I-sites of pMTBiP/V5-His B (Invitrogen).

EXAMPLE 2

Recombinant Expression of an Antibody-Like Methyl-CpG-DNA-Binding Protein

Methylated Cytosine in single stranded, but not double-stranded DNA molecules can be efficiently detected using 5-mC antibodies. To enable an antibody-like detection of double-stranded CpG-methylated DNA, a vector as described in Example 1, above, was constructed encoding a fusion protein comprising the methyl-CpG binding domain (MBD) of human methyl-CpG-binding domain 2 (MBD2), a flexible linker polypeptide and the Fc portion of human IgG1. The protein was expressed under the control of a metal-inducible promoter in Drosophila S2 Schneider-cells, and collected from the supernatant via Protein A affinity chromatography. The purified protein was expressed in high amounts (4-5 mg/L cell culture supernatant) and had the expected molecular weight of appr. 40 kDa (s. FIG. 2).

Accordingly, in detail an insect cell system was chosen for recombinant expression of MBD2-Fc protein for several reason. The main reason is the absence or low abundance of CpG-methylation. Production of the protein in mammalian (especially human) cells may result in DNA contaminations (bound to the MBD2-Fc protein in the cell culture supernatant) which may complicate subsequent analysis of CpG-methylated DNA. Other reasons include the simple culture conditions and the potentially high yields of protein.

Drosophila S2 cells were obtained from ATTC and cultured in Insect-Xpress medium (Bio Whittaker) containing 10% FCS (PAA) in an incubator at 25° C.

$4\times10^6$ Drosophila S2 cells/60 mm cell culture dish were transfected with a mixture of 1.5 µg pMTBip/MBD2-Fc and 0.3 µg pCoHygro (Invitrogen) using Effectene transfection reagent (Qiagen) according to the manufacturers protocol. On day three, transfected cells were harvested, washed and replated in selection medium (Insect-Xpress) containing 10% FCS and 300 µg/ml Hygromycin (BD Biosciences). Selection medium was replaced every 4-5 days for five weeks. The pool of stably transfected Drosophila S2 cells was expanded and several aliquots preserved in liquid nitrogen.

For large scale production, $1-5\times10^8$ cells were cultured in 100-200 ml Insect-Xpress without FCS (optional: 300 µg/ml Hygromycin) in 2000 ml roller bottles for two days before the addition of 0.5 mM $CuSO_4$. Medium was harvested every 4-7 days and cells were replated medium plus $CuSO_4$ for further protein production. Cell culture supernatants were combined, dialysed against TBS (pH 7.4) and purified using a protein A column. The MBD-Fc containing fractions were combined and dialysed against TBS (pH 7.4). The stably transfected Drosophila S2 cells produced 3-5 mg recombinant MBD2-Fc protein per litre cell culture supernatant.

EXAMPLE 3

Detection of CpG-Methylated DNA on Membranes (Reverse South-Western Blot)

To test, whether MBD2-Fc was able to detect CpG-methylated DNA on membrane in a Western blot-like procedure, we blotted in vitro methylated or unmethylated PCR-fragments with different CpG density onto a Nylon-membrane using a capillary transfer system equivalent to traditional Southern blotting, however without denaturing the DNA prior to blotting. As shown in FIG. 3, using standard immunoblot conditions and MBD-Fc as an equivalent to the primary antibody, methylated DNA can be detected on Nylon membranes in a linear fashion (FIG. 3A) and depending on the CpG content (FIG. 3B). These results indicated that the MBD-Fc fusion protein is able to detect CpG-methylated DNA bound to a solid support.

EXAMPLE 4

Small Scale Enrichment of CpG-methylated DNA Using Methyl-CpG-Immunoprecipitation (MCIp)

The following protocol allows a quick enrichment of CpG-methylated DNA fragments using spin columns. The DNA is bound to MBD2-Fc protein coupled to Sepharose beads via Protein A. The affinity for methylated DNA increases with the density of methylated CpG-dinucleotides and decreases with the ionic strength of the wash buffer.

4.1 Binding of the MBD2-Fc Protein to Protein A Sepharose 8-10 µg purified MBD2-Fc protein was added to 50 µl Protein A Sepharose 4 Fast Flow beads (Amersham) in 1 ml TBS and rotated over night on a rotator at 4° C. On the next day, MBD2-Fc-beads were washed twice with buffer A (20 mM Tris-HCl pH 8.0, 2 mM $MgCl_2$, 0.5 mM EDTA, 150 mM NaCl, 0.1% NP-40).

4.2 Restriction Digest and Quantitation of DNA

At least 1 µg genomic DNA (prepared using Qiagen columns) was digested using Mse I. Complete digest was controlled using agarose gel elecrophoresis and digested DNA was exactly quantified using PicoGreen dsDNA Quantitation Reagent (Molecular Probes).

4.3 Purification of Highly Methylated CpG-DNA

Digested DNA (300 ng) was added to the washed MBD2-Fc-beads in 1 ml buffer A and rotated for 3 h on a rotator at 4° C. Beads were transferred into SpinX-columns and spin-washed with approximately 1 ml buffer A. Beads were washed twice with 400 µl buffer B (20 mM Tris-HCl pH 8.0, 2 mM $MgCl_2$, 0.5 mM EDTA, 450 mM NaCl, 0.1% NP-40) and twice with buffer C (20 mM Tris-HCl pH 8.0, 2 mM $MgCl_2$, 0.5 mM EDTA, 650 mM NaCl, 0.1% NP-40). Flow through of each wash step was either discarded or collected for further analyses. CpG-methylated DNA was eluted with 250 µl buffer D (20 mM Tris-HCl pH 8.0, 2 mM $MgCl_2$, 0.5 mM EDTA, 1000 mM NaCl, 0.1% NP-40) into a new tube. Eluted DNA was desalted using Qiaquick Spin columns (ELUTED). In parallel, 300 ng digested DNA (INPUT) was resuspended in 250 µl buffer D and desalted using QIAquick PCR Purification Kit (Qiagen). Both ELUTED- and INPUT-DNA was exactly quantified using PicoGreen dsDNA Quantitation Reagent (Molecular Probes).

4.4. Alternative Approaches

DNA may be restricted using different restriction endonucleases or by sonication.

EXAMPLE 5

Detection and Quantitation of Methylated CpG-DNA Fragments Generated by MCIp

To test, whether the MBD-Fc fusion protein was able to bind CpG-methylated DNA fragments in an immunoprecipitation-like approach, we first tested the binding properties of in vitro generated and differentially methylated DNA-fragments. PCR fragments of human promoters with varying CpG-density were generated using PCR (s. FIG. 4) and CpG-methylated using SssI (CCL13, TLR2, CHI3L1) or left unmethylated (CPM). DNA was bound to MBD-Fc-Protein A sepharose beads in 150 mM NaCl (s. Example 4) and eluted using increasing concentrations of NaCl. Fractions were collected, spin-purified and subjected to agarose gel electrophoresis. As shown in FIG. 4B, the affinity of a methylated fragment increased with the density of methylated CpG-dinucleotide, with unmethylated DNA (CPM promoter fragment) eluting at relatively low salt concentrations and highly methylated DNA (TLR2 promoter fragment) eluting at high salt concentrations. Variation of the amount of Input-DNA did not significantly change the elution profile. However, the salt-dependent affinity of DNA was dependent on the density of the MBD-Fc fusion protein on the protein A sepharose beads. These results indicated that the MBD-Fc fusion protein is able to capture and bind CpG-methylated DNA in solution in a salt concentration- and CpG-methylation density-dependent fashion.

5.1 Quantitation on Single Gene Level Using Gene-Specific Real-Time PCR 5.1.1 To test whether the recombinant MBD-Fc protein was able to detect the methylation density of a CpG island promoter in a complex genomic DNA mixture, genomic DNA from three leukemia cell lines, normal donor monocytes as well as blast cells from a patient with AML were restricted with Mse I and subjected to MCIp. The enrichment of three CpG island promoters (TLR2, p15 and ESR1) in the 1000 mM NaCl MCIp-fraction was detected using LightCycler-PCR. The three loci were chosen because p15 and ESR1 are known targets for methylation in leukemia and TLR2 was previously shown to be methylated in U937 cells, but not in THP-1 cells. As shown in FIG. 5, none of the three loci was significantly detectable in the DNA preparation from the normal donor DNA (MO), which is consistent with a usually unmethylated state of CpG island promoters in normal cells. The enrichment of TLR2 in U937 but not in THP-1 is consistent with the previously observed methylation pattern in both cells. Bisulfite sequencing of the TLR2 promoter as described in Hähnel, J. Immunol. 168 (2002), 5629-37) demonstrated an almost complete methylation of the TLR2 promoter in KG1-cells (data not shown) which is consistent with the strong MCIp-enrichment shown in FIG. 5. The results for p15 in KG1 and U937 are consistent with published data. These data indicate that MCIp can be used to detect methylated DNA fragments of single gene fragments in genomic DNA.

Accordingly, enrichment of a specific Mse I-fragment in the MCIp eluate was detected and quantified relative to the genomic INPUT by Real-time Lightcycler-PCR. (s. FIG. 5). The enrichment may also be quantified after an unspecific DNA-amplification of both ELUTED- and INPUT-DNA (s. amplicon generation in Example 5.2.1 below, data not shown).

(ESR1) gene (Issa, Cancer Res. 56 (1996), 973-977) and the human Toll-like receptor 2 gene (TLR2) (data not show). As shown in FIG. 9C, the profiles of methylated and unmethylated DNA at the CHI3L1 locus were significantly different from those of the above tested CpG island promoters. Most of the untreated CHI3L1-fragment was recovered at lower NaCl concentrations, and a slight shift was observed towards higher NaCl concentrations when the DNA was SssI-methylated. Analysis of the above elution profiles suggests that:

a.) A two to three hundred-fold enrichment of stronger over less methylated genomic fragments can be obtained in either low or high salt fractions;
b.) Fragments with low CpG density are largely excluded from the high salt fraction.
c.) The fractionated MCIp approach allows the resolution of small differences in CpG methylation density (the average difference between SssI-treated and untreated monocyte DNA is approximately six out of twelve methylated CpG residues, data not shown);

In order to test whether MCIp can detect aberrant hypermethylation in tumor samples, DNA from three leukaemia cell lines (KG1, U937, THP-1) as well as from monocytes of a healthy donor were analyzed for SNRNP, CDKN2B, ESR1 and TLR2 promoter enrichment in the high salt fraction (s.

TABLE 1-1

Gene-specific oligonucleotide primers for CpG-island promoters

| Gene | Mse I fragment (bp) | Sense primer | Antisense primer | product (bp) |
|---|---|---|---|---|
| TLR2 | 1358 | TGTGTTTCAGGTGATGTGAGGTC (SEQ ID NO: 6) | CGAATCGAGACGCTAGAGGC (SEQ ID NO: 7) | 118 |
| p15 | 699 | GGCTCAGCTTCATTACCCTCC (SEQ ID NO: 8) | AAAGCCCGGAGCTAACGAC (SEQ ID NO: 9) | 87 |
| ESR1 | 1108 | GACTGCACTTGCTCCCGTC (SEQ ID NO: 10) | AAGAGCACAGCCCGAGGTTAG (SEQ ID NO: 11) | 129 |

In order to test whether MCIp may be used to discriminate methylated and unmethylated DNA fragments from genomic DNA, MCIp was used to enrich MseI-restricted genomic DNA of in vitro SssI-methylated and untreated normal DNA from monocytes of a healthy donor. MseI was chosen for DNA fragmentation, because it is known to preferentially cut in regions of low CpG content while leaving many CpG islands uncut (Cross, Nat. Genet. 6 (1994), 236-244).

The salt concentration-dependent enrichment of four different CpG-island promoters and a promoter with low CpG density was determined in SssI-methylated and untreated DNA relative to the input-DNA using LightCycler real-time PCR. As a positive control for DNA methylation, the SNRPN gene promoter that is subject to maternal imprinting with one of its two copies being methylated also in normal cells (Zeschnigk, Hum. Mol. Genet. 6 (1997), 387-395) was used. In normal DNA the two differentially methylated allele-fragments of SNRPN were enriched in two separate fractions (s. FIG. 9A). Only one enriched fraction was observed with SssI-methylated DNA. In the case of CDKN2B gene (also known as p15$^{INK4b}$) which is known to be frequently methylated in leukaemia cells (Chim, Ann. Hematol. 82 (2003), 738-742; Dodge, Int. J. Cancer 78 (1998), 561-567; Dodge, Leuk. Res. 25 (2001), 917-925) (FIG. 9B), the fragment was detected mainly in a low salt fraction from normal DNA and in the high salt fraction from SssI-methylated DNA. Similar results were obtained for the human estrogen receptor 1

FIG. 9D-G). The TLR2 gene promoter was enriched in KG-1 and U937 cells, but not in THP-1 or normal cells. The methylation pattern of TLR2 was confirmed by bisulfite sequencing (Haehnel, J. Immunol. 168 (2002), 5629-5637) (data not shown). Results for CDKN2B (KG-1 and U937) and ESR1 (KG-1) were also in line with previously published studies (Chim (2003); Dodge (2001); Issa (1996), all loc. cit.). None of the above three MseI fragments was significantly enriched in the DNA from normal cells. In concordance with its imprinting-related methylation status the SNRPN gene promoter was significantly enriched in all leukaemia cell lines as well as in normal cells. These experiments established that the high salt MCIp fraction specifically enriches genomic DNA-fragments with a high degree of CpG methylation.

TABLE 1-2

Gene-specific oligonucleotide primers for real-time amplification of CpG-island promoters

| Gene | Primer sequence (sense & antisense) |
|---|---|
| SNRNP | 5'-TAC ATC AGG GTG ATT GCA GTT CC-3' (SEQ ID NO: 12)<br>5'-TAC CGA TCA CTT CAC GTA CCT TCG-3' (SEQ ID NO: 13) |

TABLE 1-2-continued

Gene-specific oligonucleotide primers for
real-time amplification of CpG-island
promoters

| Gene | Primer sequence (sense & antisense) |
|---|---|
| TLR2 | 5'-TGT GTT TCA GGT GAT GTG AGG TC-3' (SEQ ID NO: 14)<br>5'-CGA ATC GAG ACG CTA GAG GC-3 (SEQ ID NO: 15)' |
| ESR1 | 5'-GAC TGC ACT TGC TCC CGT C-3' (SEQ ID NO: 16)<br>5'-AAG AGC ACA GCC CGA GGT TAG-3' (SEQ ID NO: 17) |
| CDKN2B | 5'-GGC TCA GCT TCA TTA CCC TCC-3' (SEQ ID NO: 18)<br>5'-AAA GCC CGG AGC TAA CGA C-3' (SEQ ID NO: 19) |
| CHI3L1 | 5'-ATC ACC CTA GTG GCT CTT CTG C-3' (SEQ ID NO: 20)<br>5'-CTT TTA TGG GAA CTG AGC TAT GTG TC-3' (SEQ ID NO: 21) |

5.1.2 In order to determine the amount of DNA required for the detection of a single gene fragment in a complex mixture of genomic DNA, decreasing amounts of DNA fragments were subjected to MCIp and subsequent LightCycler real-time PCR. As shown in FIG. 6, the methylated TLR2 promoter can be enriched and detected from as little as 1 ng genomic DNA from U937 cells. The un-methylated p15-promoter was not significantly enriched (20 ng MCIp-eluate) or not detectable (4 ng or 1 ng MCIp-eluate) in U937 cells (FIG. 6). These results indicate that MCIp is a sensitive method to detect methylated DNA-fragments in a complex genomic mixture.

In order to test the sensitivity of the approach, decreasing amounts of U937 DNA were analyzed using the MCIp approach. The enrichment of TLR2 (strong methylation) and CDKN2B gene fragments (no methylation) were determined by LightCycler real-time PCR. As shown in FIG. 10A, a significant enrichment of the TLR2 fragment was achieved using as little as 1 ng of genomic DNA fragments (equivalent to approximately 150 tumor cells) for the MCIp procedure. Samples derived from tumors may contain significant numbers of normal cells, that would be expected to be unmethylated at most CpG islands. To test how linear the detection of CpG methylation is with respect to cell purity, MCIp was performed using mixtures of DNA from normal blood cells and the leukaemia cell line KG-1 showing high levels of CpG island methylation at several promoters. As shown in FIG. 10B, the TLR2 promoter fragment was only detected in samples containing KG-1 DNA and the signal gradually increased with the proportion of methylated DNA in the sample. Similar results were obtained for the ESR1 locus (data not shown). In general, most informative (with respect to effects on transcription) and clearest results (in terms of noise and background) were obtained when a target gene fragment contained only the proximal promoter within the CpG island. Also, in addition to enzyme restriction, DNA fragmentation may also be achieved by mechanical means, e.g. sonication (data not shown).

5.2 Quantitation on Genome-Wide Level Using Microarray Technology 5.2.1 Generation of DNA-Amplicons from Genomic MSE I-Fragments Using Ligation-Mediated (LM)-PCR To generate a Mse I-compatible LMPCR-Linker, oligonucleotides LMPCR_S-L (5'-GCG GTG ACC CGG GAG ATC TCT TAA G-3') (SEQ ID NO: 22) and LMPCR_AS-L (5'-TAC TTA AGA GAT C-3') (SEQ ID NO: 23) were annealed as follows. Both oligos were combined at a concentration of 20 μM in nuclease-free $H_2O$ (USB), incubated at 80° C. for 10 min, and cooled down slowly to RT. The annealed Linker was stored in 50 μl-aliquots at −20° C.

LMPCR-Linker (0.5 μl/ng ELUTED- or INPUT-DNA) was ligated to the ELUTED- and in a separate reaction to an equal amount of INPUT-DNA in 60 μl reactions using 1 μl, T4-Ligase (1200 u/μl, NEB) at 16° C. o/n. Linker-ligated DNA was desalted using QIAquick PCR Purification Kit (Qiagen) and eluted in 55 μl Tris-HCl pH 8.0 (5 mM).

Linker-ligated DNA (ELUTED- and INPUT separately) was PCR-amplified using LMPCR-Primer (5'-GTG ACC CGG GAG ATC TCT TAA G-3') (SEQ ID NO: 24) and Taq DNA Polymerase (Roche). The PCR mix contained 25 μl 10×PCR-buffer (Roche), 15 μ, $MgCl_2$ (25 mM, Roche), 10 μl dNTPs (10 mM each) 65 μl Betain (5M, Sigma), 2.5 μl LMPCR-Primer, 45 μl of linker-ligated DNA, 2.5 μl Taq DNA Polymerase (5 U/μl) in a total volume of 250 μl which was distributed into five PCR-tubes. Cycling parameters were: 58° C., 2 min (melting off LMPCR_AS-L), 72° C. 5 min (fill in overhangs); 95° C., 30 s, 58° C., 30 s, 72° C., 3 min amplification for 15 cycles; 72° C., 10 min final extension.

PCR-Reactions were combined and purified using QIAquick PCR Purification Kit (Qiagen). Both ELUTED- and INPUT-amplicons were exactly quantified using PicoGreen dsDNA Quantitation Reagent (Molecular Probes).

5.2.2 Analysis of MCIp-Amplicons Using CpG-Island Microarrays

MCIp-Amplicons may be analysed using PCR (LightCycler, Standard PCR) to detect the enrichment of single gene fragments. To detect multiple gene fragments array technology may be used. The analysis of MCIp-amplicons using for example CpG island microarrays will involve the fluorescent labelling of MCIp-DNA-fragments and subsequent hybridization to microarrays using standard protocols.

EXAMPLE 6

Single-tube Assay for the Detection of CpG-methylated DNA-fragments Using Methyl-Binding Polymerase Chain Reaction (MB-PCR)

This method uses an approach similar to ELISAs. A protein with high affinity for CpG-methylated DNA is coated onto the walls of a PCR-cycler compatible reaction vessel and used to selectively capture strongly methylated DNA-fragments from a genomic DNA mixture. The retention of a specific DNA-fragment (e.g. a CpG island promoter of a specific gene) can be detected in the same tube using PCR (either standard PCR or realtime PCR, single or multiplex). The degree of methylation may be estimated relative to a PCR reaction of the genomic input DNA. FIG. 7 shows a schematic representation of MB-PCR.

6.1 DNA Preparation and Fragmentation

Genomic DNA from three cell lines (KG1, U937, and THP-1), normal human monocytes (healthy donor) and frozen blast cells from a patient with AML were prepared using Blood and Cell Culture Midi Kit (Qiagen). Quality of the genomic DNA-preparation was controlled by agarose gel electrophoresis and DNA concentration was determined by UV spectrophotometry. Genomic DNA was digested with Mse I (NEB) and finally quantified using PicoGreen dsDNA Quantitation Reagent (Molecular Probes).

6.2 Preparation of PCR Tubes

MBD-Fc-coated PCR tubes were prepared using heat stable TopYield™ Strips (Nunc Cat. No. 248909). 50 µl of recombinant MBD-Fc protein (diluted at 15 µg/ml in 10 mM Tris/HCl pH 7.5) were added to each well and incubated overnight at 4° C. Wells were washed three times with 200 µl TBS (20 mM Tris, pH 7.4 containing 150 mM NaCl) and blocked overnight at 4° C. with 100 µl Blocking Solution (10 mM Tris, pH 7.5 containing 150 mM NaCl, 4.5% skim milk powder, 5 mM EDTA and 0.8 µg/ml of each poly d(I/C), poly d(A/T and poly d(CG)). Tubes were washed three times with 200 µl TBST (TBS containing 0.1% Tween-20.

6.3 Binding of Methylated DNA

50 µl Binding Buffer (20 mM Tris, pH 7.5 containing 400 mM NaCl, 2 mM MgCl$_2$, 0.5 mM EDTA, and 0.1% Tween-20) were added to each well and 1 µl Mse I-digested DNA (10 ng/µl) was added to every second well (M-reaction). Wells were incubated on a shaker at 4° C. for 3 hours. Tubes were washed three times with 200 µl Binding Buffer and once with 10 mM Tris/HCl pH 7.5.

6.4 Detection of Methylated DNA Fragments

PCR was carried out directly in the TopYield™ Strips. The PCR-Mix (50 µl/well) contained a standard PCR buffer (Roche), 2.5 U FastStart Taq DNA Polymerase (Roche), 10 pmol of each gene-specific primer (synthesized by Qiagen), dNTPs (200 mM each, Amersham/Pharmacia) 1 M betaine (Sigma), primer sequences and cycling parameters are shown in Table 2 & 3, respectively. After adding the PCR-mix, 1 µl Mse 1-digested DNA (10 ng/µl) was added to every second other well, that was not previously incubated with DNA-fragments (P-reaction). PCR-products were analysed using agarose gel electrophoresis and the ethidium bromide stained gel was scanned using a Typhoon 9200 Imager (Amersham/Pharmacia).

TABLE 2

| Cycling parameters (MB-PCR): | | |
|---|---|---|
| 94° C. | 3 min | |
| 94° C. | 30 s | |
| 60° C. | 30 s | } 37 x |
| 72° C. | 50 s | |
| 72° C. | 5 min | |
| 15° C. | ∞ | |

TABLE 3

Gene-specific oligonucleotide primers for CpG-island promoters

| Gene | Mse I fragment (bp) | Sense primer | Antisense primer | product (bp) |
|---|---|---|---|---|
| TLR2 | 1358 | TGTGTTTCAGGTGATGTGAGGTC (SEQ ID NO: 14) | CGAATCGAGACGCTAGAGGC (SEQ ID NO: 15) | 118 |
| p15 | 699 | GGCTCAGCTTCATTACCCTCC (SEQ ID NO: 8) | AAAGCCCGGAGCTAACGAC (SEQ ID NO: 9) | 87 |
| ESR1 | 1108 | GACTGCACTTGCTCCCGTC (SEQ ID NO: 16) | AAGAGCACAGCCCGAGGTTAG (SEQ ID NO: 17) | 129 |

FIG. 8 shows the result of an MB-PCR experiment analysing the methylation profile of three different CpG-island promoters in five cell types. The lanes marked with P represent the amplification of the genomic input DNA. With an exception of the (probably deleted or mutated) p15 gene in THP-1 cells, all promoters were amplified. Notably, none of the promoters was detected in the MB-PCR reactions from the normal DNA control, which is consistent with the fact that these promoters are not methylated in normal individuals. In the cell lines as well as in the patient sample, promoters were mostly methylated. The results correspond to the data obtained with MCIp in independent experiments.

The invention claimed is:

1. A bifunctional polypeptide comprising an Fc portion of an antibody, a short flexible peptide linker, and a DNA-binding domain of an MBD2 protein, wherein the short flexible peptide linker comprises amino acids 116 to 129 of SEQ ID NO:2.

2. A composition comprising the bifunctional polypeptide of claim 1.

3. The composition of claim 2 which is a diagnostic composition.

4. The bifunctional polypeptide of claim 1, wherein the bifunctional polypeptide is capable of enriching methylated DNA from less than 10 ng of genomic DNA.

5. The bifunctional polypeptide of claim 1, wherein the MBD2 protein is a human MBD2 protein.

6. A composition comprising the bifunctional polypeptide of claim 5.

7. The composition of claim 6 which is a diagnostic composition.

8. The bifunctional polypeptide of claim 5, wherein the bifunctional polypeptide is capable of enriching methylated DNA from less than 10 ng of genomic DNA.

* * * * *

SEQUENCE LISTING

<160> NUMBER OF SEQ ID NOS: 24

<210> SEQ ID NO 1
<211> LENGTH: 4598
<212> TYPE: DNA
<213> ORGANISM: Homo sapiens
<220> FEATURE:
<221> NAME/KEY: CDS
<222> LOCATION: (851)..(1933)

```
<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccag tgaattttaa cgttgcagga     420
caggatgtgg tgcccgatgt gactagctct ttgctgcagg ccgtcctatc ctctggttcc     480
gataagagac ccagaactcc ggccccccac cgcccaccgc cacccccata catatgtggt     540
acgcaagtaa gagtgcctgc gcatgcccca tgtgccccac caagagtttt gcatcccata     600
caagtcccca agtggagaa ccgaaccaat tcttcgcggg cagaacaaaa gcttctgcac     660
acgtctccac tcgaatttgg agccggccgg cgtgtgcaaa agaggtgaat cgaacgaaag     720
acccgtgtgt aaagccgcgt ttccaaaatg tataaaaccg agagcatctg gccaatgtgc     780
atcagttgtg gtcagcagca aaatcaagtg aatcatctca gtgcaactaa agggggggatc     840 cgatctcaat atg aag tta tgc ata tta ctg gcc gtc gtg gcc ttt gtt        889
            Met Lys Leu Cys Ile Leu Leu Ala Val Val Ala Phe Val
            1               5                   10 ggc ctc tcg ctc ggg aga tct cca tgg ccc ggg gta cct act agc acg       937
Gly Leu Ser Leu Gly Arg Ser Pro Trp Pro Gly Val Pro Thr Ser Thr
 15              20                  25 gag agc ggg aag agg atg gat tgc ccg gcc ctc ccc ccc gga tgg aag       985
Glu Ser Gly Lys Arg Met Asp Cys Pro Ala Leu Pro Pro Gly Trp Lys
30              35                  40                  45 aag gag gaa gtg atc cga aaa tct ggg cta agt gct ggc aag agc gat      1033
Lys Glu Glu Val Ile Arg Lys Ser Gly Leu Ser Ala Gly Lys Ser Asp
                50                  55                  60 gtc tac tac ttc agt cca agt ggt aag aag ttc aga agc aag cct cag      1081
Val Tyr Tyr Phe Ser Pro Ser Gly Lys Lys Phe Arg Ser Lys Pro Gln
            65                  70                  75 ttg gca agg tac ctg gga aat act gtt gat ctc agc agt ttt gac ttc      1129
Leu Ala Arg Tyr Leu Gly Asn Thr Val Asp Leu Ser Ser Phe Asp Phe
        80                  85                  90 aga act gga aag atg atg cct agt aaa tta cag aag aac aaa cag aga      1177
Arg Thr Gly Lys Met Met Pro Ser Lys Leu Gln Lys Asn Lys Gln Arg
    95                 100                 105 ctg cga aac gat cct ctg gcg gcc gcg gat ccc atc gaa ggt cgt ggt      1225
Leu Arg Asn Asp Pro Leu Ala Ala Ala Asp Pro Ile Glu Gly Arg Gly
110                 115                 120                 125 ggt ggt ggt ggt gat ccc aaa tct tgt gac aaa cct cac aca tgc cca      1273
Gly Gly Gly Gly Asp Pro Lys Ser Cys Asp Lys Pro His Thr Cys Pro
                130                 135                 140 ctg tgc cca gca cct gaa ctc ctg ggg gga ccg tca gtc ttc ctc ttc      1321
Leu Cys Pro Ala Pro Glu Leu Leu Gly Gly Pro Ser Val Phe Leu Phe
            145                 150                 155 ccc cca aaa ccc aag gac acc ctc atg atc tcc cgg acc cct gag gtc      1369
Pro Pro Lys Pro Lys Asp Thr Leu Met Ile Ser Arg Thr Pro Glu Val
        160                 165                 170 aca tgc gtg gtg gtg gac gtg agc cac gaa gac cct gag gtc aag ttc      1417
Thr Cys Val Val Val Asp Val Ser His Glu Asp Pro Glu Val Lys Phe
    175                 180                 185 aac tgg tac gtg gac ggc gtg gag gtg cat aat gcc aag aca aag ccg      1465
```

-continued

| | | |
|---|---|---|
| Asn Trp Tyr Val Asp Gly Val Glu Val His Asn Ala Lys Thr Lys Pro<br>190                   195                   200                   205 | |

```
cgg gag gag cag tac aac agc acg tac cgt gtg gtc agc gtc ctc acc      1513
Arg Glu Glu Gln Tyr Asn Ser Thr Tyr Arg Val Val Ser Val Leu Thr
                    210                 215                 220 gtc ctg cac cag gac tgg ctg aat ggc aag gag tac aag tgc aag gtc      1561
Val Leu His Gln Asp Trp Leu Asn Gly Lys Glu Tyr Lys Cys Lys Val
                225                 230                 235 tcc aac aaa gcc ctc cca gcc ccc atc gag aaa acc atc tcc aaa gcc      1609
Ser Asn Lys Ala Leu Pro Ala Pro Ile Glu Lys Thr Ile Ser Lys Ala
            240                 245                 250 aaa ggg cag ccc cga gaa cca cag gtg tac acc ctg ccc cca tcc cgg      1657
Lys Gly Gln Pro Arg Glu Pro Gln Val Tyr Thr Leu Pro Pro Ser Arg
        255                 260                 265 gat gag ctg acc aag aac cag gtc agc ctg acc tgc cta gtc aaa ggc      1705
Asp Glu Leu Thr Lys Asn Gln Val Ser Leu Thr Cys Leu Val Lys Gly
270                 275                 280                 285 ttc tat ccc agc gac atc gcc gtg gag tgg gag agc aat ggg cag ccg      1753
Phe Tyr Pro Ser Asp Ile Ala Val Glu Trp Glu Ser Asn Gly Gln Pro
                    290                 295                 300 gag aac aac tac aag gcc acg cct ccc gtg ctg gac tcc gac ggc tcc      1801
Glu Asn Asn Tyr Lys Ala Thr Pro Pro Val Leu Asp Ser Asp Gly Ser
                305                 310                 315 ttc ttc ctc tac agc aag ctc acc gtg gac aag agc agg tgg cag cag      1849
Phe Phe Leu Tyr Ser Lys Leu Thr Val Asp Lys Ser Arg Trp Gln Gln
            320                 325                 330 ggg aac gtc ttc tca tgc tcc gtg atg cat gag gct ctg cac aac cac      1897
Gly Asn Val Phe Ser Cys Ser Val Met His Glu Ala Leu His Asn His
        335                 340                 345 tac acg cag aag agc ctc tcc ctg tct ccg ggt aaa tgagctagag           1943
Tyr Thr Gln Lys Ser Leu Ser Leu Ser Pro Gly Lys
350                 355                 360
```

```
ggcccgcggt tcgaaggtaa gcctatccct aaccctctcc tcggtctcga ttctacgcgt    2003
accggtcatc atcaccatca ccattgagtt taaacccgct gatcagcctc gactgtgcct    2063
tctaaggcct gagctcgctg atcagcctcg atcgaggatc cagacatgat aagatacatt    2123
gatgagtttg gacaaaccac aactagaatg cagtgaaaaa aatgctttat ttgtgaaatt    2183
tgtgatgcta ttgctttatt tgtaaccatt ataagctgca ataaacaagt taacaacaac    2243
aattgcattc attttatgtt tcaggttcag ggggaggtgt gggaggtttt ttaaagcaag    2303
taaaacctct acaaatgtgg tatggctgat tatgatcagt cgacctgcag gcatgcaagc    2363
ttggcgtaat catggtcata gctgtttcct gtgtgaaatt gttatccgct cacaattcca    2423
cacaacatac gagccggaag cataaagtgt aaagcctggg gtgcctaatg agtgagctaa    2483
ctcacattaa ttgcgttgcg ctcactgccc gctttccagt cgggaaacct gtcgtgccag    2543
ctgcattaat gaatcggcca acgcgcgggg agaggcggtt tgcgtattgg gcgctcttcc    2603
gcttcctcgc tcactgactc gctgcgctcg gtcgttcggc tgcggcgagc ggtatcagct    2663
cactcaaagg cggtaatacg gttatccaca gaatcagggg ataacgcagg aaagaacatg    2723
tgagcaaaag gccagcaaaa ggccaggaac cgtaaaaagg ccgcgttgct ggcgtttttc    2783
cataggctcc gccccctga  cgagcatcac aaaaatcgac gctcaagtca gaggtggcga    2843
aacccgacag gactataaag ataccaggcg tttccccctg gaagctccct cgtgcgctct    2903
cctgttccga ccctgccgct taccggatac ctgtccgcct ttctcccttc gggaagcgtg    2963
gcgctttctc atagctcacg ctgtaggtat ctcagttcgg tgtaggtcgt tcgctccaag    3023
```

|  |  |
|---|---:|
| ctgggctgtg tgcacgaacc ccccgttcag cccgaccgct gcgccttatc cggtaactat | 3083 |
| cgtcttgagt ccaacccggt aagacacgac ttatcgccac tggcagcagc cactggtaac | 3143 |
| aggattagca gagcgaggta tgtaggcggt gctacagagt tcttgaagtg gtggcctaac | 3203 |
| tacggctaca ctagaaggac agtatttggt atctgcgctc tgctgaagcc agttaccttc | 3263 |
| ggaaaaagag ttggtagctc ttgatccggc aaacaaacca ccgctggtag cggtggtttt | 3323 |
| tttgtttgca agcagcagat tacgcgcaga aaaaaggat ctcaagaaga tcctttgatc | 3383 |
| ttttctacgg ggtctgacgc tcagtggaac gaaaactcac gttaagggat tttggtcatg | 3443 |
| agattatcaa aaaggatctt cacctagatc cttttaaatt aaaaatgaag ttttaaatca | 3503 |
| atctaaagta tatatgagta aacttggtct gacagttacc aatgcttaat cagtgaggca | 3563 |
| cctatctcag cgatctgtct atttcgttca tccatagttg cctgactccc cgtcgtgtag | 3623 |
| ataactacga tacgggaggg cttaccatct ggccccagtg ctgcaatgat accgcgagac | 3683 |
| ccacgctcac cggctccaga tttatcagca ataaaccagc cagccggaag ggccgagcgc | 3743 |
| agaagtggtc ctgcaacttt atccgcctcc atccagtcta ttaattgttg ccgggaagct | 3803 |
| agagtaagta gttcgccagt taatagtttg cgcaacgttg ttgccattgc tacaggcatc | 3863 |
| gtggtgtcac gctcgtcgtt tggtatggct tcattcagct ccggttccca acgatcaagg | 3923 |
| cgagttacat gatcccccat gttgtgcaaa aaagcggtta gctccttcgg tcctccgatc | 3983 |
| gttgtcagaa gtaagttggc cgcagtgtta tcactcatgg ttatggcagc actgcataat | 4043 |
| tctcttactg tcatgccatc cgtaagatgc ttttctgtga ctggtgagta ctcaaccaag | 4103 |
| tcattctgag aatagtgtat gcggcgaccg agttgctctt gcccggcgtc aatacgggat | 4163 |
| aataccgcgc cacatagcag aactttaaaa gtgctcatca ttggaaaacg ttcttcgggg | 4223 |
| cgaaaactct caaggatctt accgctgttg agatccagtt cgatgtaacc cactcgtgca | 4283 |
| cccaactgat cttcagcatc ttttactttc accagcgttt ctgggtgagc aaaaacagga | 4343 |
| aggcaaaatg ccgcaaaaaa gggaataagg gcgacacgga aatgttgaat actcatactc | 4403 |
| ttcctttttc aatattattg aagcatttat cagggttatt gtctcatgag cggatacata | 4463 |
| tttgaatgta tttagaaaaa taaacaaata ggggttccgc gcacatttcc ccgaaaagtg | 4523 |
| ccacctgacg tctaagaaac cattattatc atgacattaa cctataaaaa taggcgtatc | 4583 |
| acgaggccct ttcgt | 4598 |

<210> SEQ ID NO 2
<211> LENGTH: 361
<212> TYPE: PRT
<213> ORGANISM: Homo sapiens

<400> SEQUENCE: 2

Met Lys Leu Cys Ile Leu Leu Ala Val Val Ala Phe Val Gly Leu Ser
1               5                   10                  15

Leu Gly Arg Ser Pro Trp Pro Gly Val Pro Thr Ser Thr Glu Ser Gly
                20                  25                  30

Lys Arg Met Asp Cys Pro Ala Leu Pro Pro Gly Trp Lys Lys Glu Glu
            35                  40                  45

Val Ile Arg Lys Ser Gly Leu Ser Ala Gly Lys Ser Asp Val Tyr Tyr
        50                  55                  60

Phe Ser Pro Ser Gly Lys Lys Phe Arg Ser Lys Pro Gln Leu Ala Arg
65                  70                  75                  80

Tyr Leu Gly Asn Thr Val Asp Leu Ser Ser Phe Asp Phe Arg Thr Gly
                85                  90                  95

```
Lys Met Met Pro Ser Lys Leu Gln Lys Asn Lys Gln Arg Leu Arg Asn
                100                 105                 110

Asp Pro Leu Ala Ala Asp Pro Ile Glu Gly Arg Gly Gly Gly Gly
            115                 120                 125

Gly Asp Pro Lys Ser Cys Asp Lys Pro His Thr Cys Pro Leu Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Ala Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360

<210> SEQ ID NO 3
<211> LENGTH: 361
<212> TYPE: PRT
<213> ORGANISM: Homo sapiens

<400> SEQUENCE: 3

Met Lys Leu Cys Ile Leu Leu Ala Val Val Ala Phe Val Gly Leu Ser
1               5                   10                  15

Leu Gly Arg Ser Pro Trp Pro Gly Val Pro Thr Ser Thr Glu Ser Gly
            20                  25                  30

Lys Arg Met Asp Cys Pro Ala Leu Pro Pro Gly Trp Lys Lys Glu Glu
        35                  40                  45

Val Ile Arg Lys Ser Gly Leu Ser Ala Gly Lys Ser Asp Val Tyr Tyr
    50                  55                  60

Phe Ser Pro Ser Gly Lys Lys Phe Arg Ser Lys Pro Gln Leu Ala Arg
65                  70                  75                  80

Tyr Leu Gly Asn Thr Val Asp Leu Ser Ser Phe Asp Phe Arg Thr Gly
                85                  90                  95

Lys Met Met Pro Ser Lys Leu Gln Lys Asn Lys Gln Arg Leu Arg Asn
```

```
            100                 105                 110
Asp Pro Leu Ala Ala Asp Pro Ile Glu Gly Arg Gly Gly Gly
        115                 120                 125
Gly Asp Pro Lys Ser Cys Asp Lys Pro His Thr Cys Pro Leu Cys Pro
    130                 135                 140
Ala Pro Glu Leu Leu Gly Gly Pro Ser Val Phe Leu Phe Pro Pro Lys
145                 150                 155                 160
Pro Lys Asp Thr Leu Met Ile Ser Arg Thr Pro Glu Val Thr Cys Val
                165                 170                 175
Val Val Asp Val Ser His Glu Asp Pro Glu Val Lys Phe Asn Trp Tyr
            180                 185                 190
Val Asp Gly Val Glu Val His Asn Ala Lys Thr Lys Pro Arg Glu Glu
        195                 200                 205
Gln Tyr Asn Ser Thr Tyr Arg Val Val Ser Val Leu Thr Val Leu His
    210                 215                 220
Gln Asp Trp Leu Asn Gly Lys Glu Tyr Lys Cys Lys Val Ser Asn Lys
225                 230                 235                 240
Ala Leu Pro Ala Pro Ile Glu Lys Thr Ile Ser Lys Ala Lys Gly Gln
                245                 250                 255
Pro Arg Glu Pro Gln Val Tyr Thr Leu Pro Pro Ser Arg Asp Glu Leu
            260                 265                 270
Thr Lys Asn Gln Val Ser Leu Thr Cys Leu Val Lys Gly Phe Tyr Pro
        275                 280                 285
Ser Asp Ile Ala Val Glu Trp Glu Ser Asn Gly Gln Pro Glu Asn Asn
    290                 295                 300
Tyr Lys Ala Thr Pro Pro Val Leu Asp Ser Asp Gly Ser Phe Phe Leu
305                 310                 315                 320
Tyr Ser Lys Leu Thr Val Asp Lys Ser Arg Trp Gln Gln Gly Asn Val
                325                 330                 335
Phe Ser Cys Ser Val Met His Glu Ala Leu His Asn His Tyr Thr Gln
            340                 345                 350
Lys Ser Leu Ser Leu Ser Pro Gly Lys
        355                 360

<210> SEQ ID NO 4
<211> LENGTH: 28
<212> TYPE: DNA
<213> ORGANISM: artificial sequence
<220> FEATURE:
<223> OTHER INFORMATION: Primer, human MBD2 gene

<400> SEQUENCE: 4
agatgctagc acggagagcg ggaagagg                                    28

<210> SEQ ID NO 5
<211> LENGTH: 35
<212> TYPE: DNA
<213> ORGANISM: artificial sequence
<220> FEATURE:
<223> OTHER INFORMATION: Primer, human MBD2 gene

<400> SEQUENCE: 5
atcacgcggc cgccagagga tcgtttcgca gtctc                            35

<210> SEQ ID NO 6
<211> LENGTH: 23
<212> TYPE: DNA
<213> ORGANISM: artificial sequence
```

```
<220> FEATURE:
<223> OTHER INFORMATION: Primer, human TLR2 gene

<400> SEQUENCE: 6
tgtgtttcag gtgatgtgag gtc                                              23

<210> SEQ ID NO 7
<211> LENGTH: 20
<212> TYPE: DNA
<213> ORGANISM: artificial sequence
<220> FEATURE:
<223> OTHER INFORMATION: Primer, human TLR2 gene

<400> SEQUENCE: 7
cgaatcgaga cgctagaggc                                                  20

<210> SEQ ID NO 8
<211> LENGTH: 21
<212> TYPE: DNA
<213> ORGANISM: artificial sequence
<220> FEATURE:
<223> OTHER INFORMATION: Primer, human p15 gene

<400> SEQUENCE: 8
ggctcagctt cattaccctc c                                                21

<210> SEQ ID NO 9
<211> LENGTH: 19
<212> TYPE: DNA
<213> ORGANISM: artificial sequence
<220> FEATURE:
<223> OTHER INFORMATION: Primer, human p15 gene

<400> SEQUENCE: 9
aaagcccgga gctaacgac                                                   19

<210> SEQ ID NO 10
<211> LENGTH: 19
<212> TYPE: DNA
<213> ORGANISM: artificial sequence
<220> FEATURE:
<223> OTHER INFORMATION: Primer, human ESR 1 gene

<400> SEQUENCE: 10
gactgcactt gctcccgtc                                                   19

<210> SEQ ID NO 11
<211> LENGTH: 21
<212> TYPE: DNA
<213> ORGANISM: artificial sequence
<220> FEATURE:
<223> OTHER INFORMATION: Primer, human ESR 1 gene

<400> SEQUENCE: 11
aagagcacag cccgaggtta g                                                21

<210> SEQ ID NO 12
<211> LENGTH: 23
<212> TYPE: DNA
<213> ORGANISM: artificial sequence
<220> FEATURE:
<223> OTHER INFORMATION: Primer, human SNRNP gene

<400> SEQUENCE: 12
tacatcaggg tgattgcagt tcc                                              23
```

<210> SEQ ID NO 13
<211> LENGTH: 24
<212> TYPE: DNA
<213> ORGANISM: artificial sequence
<220> FEATURE:
<223> OTHER INFORMATION: Primer, human SNRNP gene

<400> SEQUENCE: 13
taccgatcac ttcacgtacc ttcg                                          24

<210> SEQ ID NO 14
<211> LENGTH: 23
<212> TYPE: DNA
<213> ORGANISM: artificial sequence
<220> FEATURE:
<223> OTHER INFORMATION: Primer, human TLR2 gene

<400> SEQUENCE: 14
tgtgtttcag gtgatgtgag gtc                                           23

<210> SEQ ID NO 15
<211> LENGTH: 20
<212> TYPE: DNA
<213> ORGANISM: artificial sequence
<220> FEATURE:
<223> OTHER INFORMATION: Primer, human TLR2 gene

<400> SEQUENCE: 15
cgaatcgaga cgctagaggc                                               20

<210> SEQ ID NO 16
<211> LENGTH: 19
<212> TYPE: DNA
<213> ORGANISM: artificial sequence
<220> FEATURE:
<223> OTHER INFORMATION: Primer, human ESR1 gene

<400> SEQUENCE: 16
gactgcactt gctcccgtc                                                19

<210> SEQ ID NO 17
<211> LENGTH: 21
<212> TYPE: DNA
<213> ORGANISM: artificial sequence
<220> FEATURE:
<223> OTHER INFORMATION: Primer, human ESR1 gene

<400> SEQUENCE: 17
aagagcacag cccgaggtta g                                             21

<210> SEQ ID NO 18
<211> LENGTH: 21
<212> TYPE: DNA
<213> ORGANISM: artificial sequence
<220> FEATURE:
<223> OTHER INFORMATION: Primer, human CDKN2B gene

<400> SEQUENCE: 18
ggctcagctt cattaccctc c                                             21

```
<210> SEQ ID NO 19
<211> LENGTH: 19
<212> TYPE: DNA
<213> ORGANISM: artificial sequence
<220> FEATURE:
<223> OTHER INFORMATION: Primer, human CDKN2B gene

<400> SEQUENCE: 19
aaagcccgga gctaacgac                                                19

<210> SEQ ID NO 20
<211> LENGTH: 22
<212> TYPE: DNA
<213> ORGANISM: artificial sequence
<220> FEATURE:
<223> OTHER INFORMATION: Primer, human CHI3L1 gene

<400> SEQUENCE: 20
atcaccctag tggctcttct gc                                            22

<210> SEQ ID NO 21
<211> LENGTH: 26
<212> TYPE: DNA
<213> ORGANISM: artificial sequence
<220> FEATURE:
<223> OTHER INFORMATION: Primer, human CHI3L1 gene

<400> SEQUENCE: 21
cttttatggg aactgagcta tgtgtc                                        26

<210> SEQ ID NO 22
<211> LENGTH: 24
<212> TYPE: DNA
<213> ORGANISM: artificial sequence
<220> FEATURE:
<223> OTHER INFORMATION: artificial LMPCR linker oligonucleotide

<400> SEQUENCE: 22
gcggtgaccc gggagatctc ttaa                                          24

<210> SEQ ID NO 23
<211> LENGTH: 13
<212> TYPE: DNA
<213> ORGANISM: artificial sequence
<220> FEATURE:
<223> OTHER INFORMATION: artificial LMPCR linker oligonucleotide

<400> SEQUENCE: 23
tacttaagag atc                                                      13

<210> SEQ ID NO 24
<211> LENGTH: 22
<212> TYPE: DNA
<213> ORGANISM: artificial sequence
<220> FEATURE:
<223> OTHER INFORMATION: artificial LMPCR linker oligonucleotide

<400> SEQUENCE: 24
gtgacccggg agatctctta ag                                            22
```